(12) United States Patent
Fox

(10) Patent No.: US 10,512,459 B2
(45) Date of Patent: Dec. 24, 2019

(54) BONE STAPLE, INSTRUMENT AND METHOD OF USE AND MANUFACTURING

(76) Inventor: William Casey Fox, Pipe Creek, TX (US)

(*) Notice: Subject to any disclaimer, the term of this patent is extended or adjusted under 35 U.S.C. 154(b) by 0 days.

(21) Appl. No.: 13/192,162

(22) Filed: Jul. 27, 2011

(65) Prior Publication Data
US 2013/0030437 A1 Jan. 31, 2013

(51) Int. Cl.
*A61B 17/064* (2006.01)
*A61B 17/10* (2006.01)
(Continued)

(52) U.S. Cl.
CPC ........ *A61B 17/0642* (2013.01); *A61B 17/064* (2013.01); *A61B 17/0682* (2013.01); *A61B 17/10* (2013.01); *A61B 17/0644* (2013.01); *A61B 17/07207* (2013.01); *A61B 17/105* (2013.01); *A61B 17/115* (2013.01); *A61B 17/68* (2013.01); *A61B 2017/00526* (2013.01);
(Continued)

(58) Field of Classification Search
CPC .............. A61B 17/068; A61B 17/0642; A61B 17/064; A61B 17/0644; A61B 17/0682; A61B 17/68; A61B 17/072; A61B 17/07207; A61B 17/115; A61B 17/10; A61B 2017/07214; A61B 2017/00867
USPC ....... 606/71, 75, 76, 78, 151, 219, 280, 286, 606/297, 300, 311, 324, 326, 327, 329, 606/330, 331, 157, 221; 128/831, 834; 227/19, 82, 175.1, 176.1, 147
See application file for complete search history.

(56) References Cited

U.S. PATENT DOCUMENTS 2,931,038 A 4/1960 Wandel
3,225,996 A 12/1965 Mallina
(Continued)

FOREIGN PATENT DOCUMENTS

WO 2013016633 A1 1/2013

OTHER PUBLICATIONS

Wright Medical; Charlotte Foot and Ankle Fixation System Brochure, SO 040-105 Rev. 04.06 (no month, 2005); Wright Medical Technology, Inc.; US.
(Continued)

*Primary Examiner* — David W Bates
*Assistant Examiner* — Marcela I Shirsat
(74) *Attorney, Agent, or Firm* — Dickinson Wright PLLC; Ross Spencer Garsson

(57) ABSTRACT

A new shape changing staple and instrument for the fixation of structures to include bone tissue and industrial materials. This new staple stores elastic mechanical energy to exert force on fixated structures to enhance their security and in bone affect its healing response. This staple once placed changes shape in response to geometric changes in the materials structure, including healing bone tissue. The staple is advanced over prior staples due to its: 1) method of operation, 2) high strength, 3) method of insertion, 4) compressive force temperature independence, 5) energy storing staple retention and delivery system, 6) compatibility with reusable or single use product configuration, 7) efficient and cost effective manufacturing methods, and 8) reduction in the steps required to place the device. In addition to the staple's industrial application an embodiment for use in the fixation of the musculoskeletal system is shown with staple, cartridge, and extrusion handle.

11 Claims, 12 Drawing Sheets

(51) Int. Cl.
*A61B 17/068* (2006.01)
*A61B 17/68* (2006.01)
*A61B 17/072* (2006.01)
*A61B 17/00* (2006.01)
*A61B 17/115* (2006.01)

(52) U.S. Cl.
CPC .............. *A61B 2017/00867* (2013.01); *A61B 2017/0645* (2013.01); *A61B 2017/0688* (2013.01); *A61B 2017/07214* (2013.01); *Y10T 29/49874* (2015.01)

(56) References Cited

U.S. PATENT DOCUMENTS

| | | | |
|---|---|---|---|
| 3,939,828 A | | 2/1976 | Mohr et al. |
| 3,960,147 A | | 6/1976 | Murray |
| 4,265,226 A | * | 5/1981 | Cassimally .......... A61B 17/068 227/108 |
| 4,414,967 A | | 11/1983 | Shapiro |
| 4,415,111 A | * | 11/1983 | McHarrie .............. A61B 17/10 227/147 |
| 4,438,769 A | | 3/1984 | Pratt et al. |
| 4,444,181 A | | 4/1984 | Weaver et al. |
| 4,527,726 A | | 7/1985 | Assel et al. |
| 4,540,110 A | | 9/1985 | Bent et al. |
| 4,665,906 A | | 5/1987 | Jervis |
| 4,841,960 A | | 6/1989 | Garner |
| 5,067,957 A | | 11/1991 | Jervis |
| 5,246,443 A | | 9/1993 | Mai |
| 5,449,359 A | | 9/1995 | Groiso |
| 5,474,557 A | | 12/1995 | Mai |
| 5,779,707 A | | 7/1998 | Berlolet et al. |
| 5,853,414 A | | 12/1998 | Groiso |
| 6,001,110 A | * | 12/1999 | Adams .......................... 606/151 |
| 6,059,787 A | | 5/2000 | Allen |
| 6,193,733 B1 | | 2/2001 | Adams |
| 6,268,589 B1 | | 7/2001 | Flot |
| 6,323,461 B2 | | 11/2001 | Flot |
| 6,325,805 B1 | * | 12/2001 | Ogilvie et al. .................. 606/75 |
| 6,348,054 B1 | | 2/2002 | Allen |
| 6,530,933 B1 | * | 3/2003 | Yeung et al. ................. 606/151 |
| 6,685,708 B2 | | 2/2004 | Monassevitch et al. |
| 6,783,531 B2 | | 8/2004 | Allen |
| 7,240,677 B2 | | 7/2007 | Fox |
| 7,618,441 B2 | | 11/2009 | Groiso |
| 7,635,367 B2 | | 12/2009 | Groiso |
| 7,828,189 B2 | | 11/2010 | Holsten et al. |
| 8,393,517 B2 | * | 3/2013 | Milo .......................... 227/181.1 |
| 8,596,514 B2 | | 12/2013 | Miller et al. |
| 2005/0055027 A1 | * | 3/2005 | Yeung et al. .................... 606/75 |
| 2005/0096660 A1 | * | 5/2005 | Allen .............................. 606/75 |
| 2005/0273108 A1 | | 12/2005 | Groiso |
| 2006/0058796 A1 | | 3/2006 | Hartdegen et al. |
| 2006/0142771 A1 | * | 6/2006 | Beutter ............................ 606/75 |
| 2007/0093839 A1 | * | 4/2007 | Beckendorf et al. ........... 606/75 |
| 2008/0082126 A1 | * | 4/2008 | Murray et al. ................ 606/221 |
| 2010/0023062 A1 | | 1/2010 | Faillace et al. |
| 2010/0036430 A1 | | 2/2010 | Harldegen et al. |
| 2010/0125275 A1 | | 5/2010 | Kinmon et al. |
| 2010/0193569 A1 | | 8/2010 | Yates et al. |
| 2010/0237128 A1 | * | 9/2010 | Miller ................ A61B 17/0642 227/175.1 |

OTHER PUBLICATIONS

Biopro, Inc.; The BioPro Memory Staple Brochure, Brochure No. 17704, rev. 2, (May 2010); BioPro; US.

Depuy Orthopaedics, Inc.; Memory Staple Brochure, Brochure 0612-00-584 (Rev. 1) (no month, 2006); DePuy Orthopaedics, Inc.; US.

MMI-USA, Easy Clip SI SuperElastic Fixation System Brochure, ECLP1000-rev D (Aug. 12, 2009); Memometal Inc., a Memometal Technologies, Inc, company; US.

Biomedical Enterprises, Inc., OSStaple Brochure, Brochure No. A108-076 (Rev B); (No month 2010); BioMedical Enterprises, Inc.; US.

Patent Cooperation Treaty; PCT International Search Report, Issued in connection with PCT/US2012/048539; dated Oct. 18, 2012; 4 pages; US.

Patent Cooperation Treaty; PCT Written Opinion of the International Searching Authority, Issued in with connection with PCT/US2012/048539; dated Oct. 18, 2012; 19 pages; US.

S.J. Warden et al.; Mechanotransduction in cortical bone is most efficient at loading frequencies of 5-10 Hz; Nov. 7, 2003; pp. 261-270; Elsevier Inc.; US.

C.H. Turner et al.; Basic Biomechanical Measurements of Bone: A Tutorial; (no month, 1993); pp. 595-608; Pergamon Press Ltd.; US.

Clinton T. Rubin et al.; Regulation of Bone Mass by Mechanical Strain Magnitude; (no month, 1985); pp. 411-417; Calcified Tissue International; US.

Alexander G. Robling et al.; Biomechanical and Molecular Regulation of Bone Remodeling; Apr. 3, 2006; pp. 455-489; The Annual Review of Biomedical Engineering; US.

Rich Lipschutz et al.; 510K Summary of Safety and Effectiveness, Fx Devices POGO Screw; Oct. 10, 2008; 5 pages; US.

Edmund Y.S. Chao et al.; Biophysical Stimulation of Bone Fracture Repair, Regeneration and Remodelling; (no month, 2003); pp. 72-85; vol. 6; European Cells and Materials; US.

A. Chamay et al.; Mechanical Influences in Bone Remodeling, Experimental Research on Wolff's Law; (no month, 1972); pp. 172-180; vol. 5; J. Biomechanics; Great Britain.

* cited by examiner ns to pull

BONE STAPLE, INSTRUMENT AND METHOD OF USE AND MANUFACTURING

TECHNICAL FIELD

This application relates to staples used for fixation of bone and soft tissue of the musculoskeletal system and the methods for their use and more specifically to staples that are caused to change shape through their metallurgic properties and their interaction with mechanical instruments to pull together and compress bone.

BACKGROUND

Bone staples have been in clinical use for decades. These important bone fixation devices have evolved from rigid stainless steel or cobalt-chromium U-shaped implants to staples that could be manipulated to compress two adjacent bone segments.

The early rigid staples were commonly hammered into bone where the more modern devices are implanted in drilled holes and use heat or mechanical means to cause the staple to change shape and pull together and in some designs compress the bony segments. Bone staple technology used to pull bone together includes: 1) staples that are bent by an instrument: BENDABLE STAPLES, 2) heat sensitive shape memory alloy staples: MEMORY STAPLES, and 3) mechanical elastic bone staples: ELASTIC STAPLES.

The staple embodiments of this invention have advantages over the prior art because it stores mechanical energy and imparts that energy to bone through shape change and predictable bone-to-bone compression. The staple embodiments of this invention pull together and compress bone to promote healing. The prior art implants may change shape or be caused to change shape but do not pull together and compress bone with a predicable amount of shape change and compression force.

Instruments, to implant staples into bone, complement the staple's method of action. BENDABLE STAPLES use pliers, forceps, and complex instruments to apply the bending force. MEMORY STAPLES must be kept cold for body temperature heating or use an electrical resistive heating instrument to transition their crystalline structure from martensitic to austenitic. Prior ELASTIC STAPLES use pliers, hooks, forceps, and complex instruments to stretch and hold their shape while being implanted. These designs cause the surgeon to need to manipulate the implant while trying to implant it in bone. Thus these implants were difficult to implant or required complex expensive instruments thus impeding their use.

As will be clear in the following detailed description of the prior art, the embodiments illustrated of the subject invention overcome the prior art deficiencies in ease of use, manufacturing, mode of operation, strength, cost and allows hospital procedures that limit disease transmission.

Bendable Staples

Bendable staple designs use an instrument to bend the staple to facilitate placement, retention and bone movement. These designs can be bent to pull the bone together but partially spring open and provide no bone-to-bone compression.

Murray, in U.S. Pat. No. 3,960,147 uses pliers to squeeze the bridge of a staple to toe it in to enhance fixation. Weaver, in U.S. Pat. No. 4,444,181 uses a dual bridge staple and pliers to decrease the distance between the legs of a staple when the dual bridge is squeezed together. Garner, in U.S. Pat. No. 4,841,960 uses pliers to squeeze the bridge of a staple to bring the legs together.

Groiso, in U.S. Pat. Nos. 5,853,414, 5,449,359 and 7,635,367 uses pliers to bend a dual bridge titanium alloy or stainless steel staple, widening the bridge to shorten the distance between the legs and narrowing the bridge to lengthen the leg distance. Groiso calls this bending or permanent deformation "elastic" behavior when in fact this bending is mostly plastic deformation. Stainless steel and titanium alloy's elastic behavior is characterized by the 2% offset yield strength. Thus when bent with pliers or forceps the material undergoes both elastic (recoverable) and plastic (permanent) deformation. This elastic behavior under strain causes the staple to partially return to its pre-bent shape. The staple legs thus partially "spring back" and thus this type of staple does not cause bone segment compression once the pliers are no longer bending the staple. Groiso, in published continuation application Ser. No. 11/197,174 adds nitinol and shape memory features to his staple.

Hardengen, in published Application Ser. No. 10/940,396 also uses pliers and in its continuation application Ser. No. 12/582,210 Hardengen describes shape memory metal to widen the dual bridge screw plate of its parent application. Hardengen's invention is embodied in the Charlotte Staple and described in the Wright Medical, Charlotte Foot and Ankle Fixation System, page 4 and 6 document number SO 040-105 Rev. 04.06

These bendable implants bring the bone together, allow it to partially spring apart and provide no compression once the instrument is removed. They store no mechanical energy. They cannot continue to change shape to pull the bone together if a gap occurs during healing. This gap can result in delayed or non-healing. Consequently, with this impaired healing observation clinical demand for this type of bone staple has decreased. The embodiments of the subject invention of this patent overcomes the deficiencies of the bendable staples by not requiring manipulation of the implant and by storing shape changing elastic mechanical energy that continuously applies force to bone to pull it together and compress.

Memory Staples

Memory staples fabricated from the nickel-titanium alloy, nitinol, exhibit a shape memory effect when heated within their martensitic and austenitic microstructure temperature transition range. A U-shaped implant can be fabricated so that it returns to a predetermined final shape. Traditionally these implants have parallel legs and then when heated the legs change shape at the corners of the U-shaped bridge to bring the tips of the legs together so as to lock in bone and in some designs create bony compression. The bridge of these staples often have a geometry capable of changing shape so it can be shortened to provide further bony compression. These heat sensitive implants can have their shape change temperature varied by changes in their composition, residual stress in the material and heat treatment.

Mai, U.S. Pat. No. 5,246,443 used a martensitic to austenitic transition temperature of 10° C. to 15° C. and described a number of bone staples and plates and relied on body heat to initiate the transformation. Mai, in U.S. Pat. No. 5,474,557 presented a temperature transition range of −20° C. to 70° C. of which temperatures over 37° C. exceed body temperature and further described other staples, plates and clips. Bertolet, in U.S. Pat. No. 5,779,707 introduced shape changing holes and slots to shorten the bridge section of plates, staples and clips but again used martensitic to austenitic transformations at body temperature to affect their shape. Ogilvie, U.S. Pat. Nos. 6,325,805 and 6,773,437 expanded the use of body temperature staples for correction of spinal deformity.

These heat sensitive staples that rely on microstructure transition are problematic because during implantation the staple is in its mechanically soft martensitic state and commonly deform inappropriately with the impaction of surgical placement. Furthermore, during shipping, costly strategies must be implemented to keep environmental heating from causing the staple to change shape prior to implantation. Finally, a heating strategy must be used to activate the implant.

Originally heat sensitive nitinol staples were activated with the temperature of the human body, approximately 37° C. This strategy and implant formulation caused critical issues by changing shape and applying bone fixation forces only after the surgical wound had been closed and allowed to warm to normal body temperature. This post surgery shape change was reported to cause deformity and fracture. This style of nitinol staple was further inconvenient in its use because the transition temperature began at below room temperature thus these implants were changing shape while being implanted by the surgeon. Strategies such as keeping the staple on dry ice were used to partially overcome this issue but it added cost and the surgeon had to work quickly in procedures where deliberate and detailed technique was required.

The body temperature nitinol staples are further described in Biopro, Inc.'s Memory Staple Brochure, and Depuy Inc.'s Memory Staple Brochure. The review of the prior art patent, technical and sales literature it is clear that the cost, inconvenience and risk of use of body temperature staples have impeded clinical adoption due to complications.

Staples that changed shape at temperatures above body temperature were developed to avoid the implant changing shape during surgery and to provide shape change and force control of the implant. Fox, U.S. Pat. No. 7,240,677 used a controlled amount of electrical current passed through the metal to resistively heat staples above body temperature to convert the martensitic crystalline structure to austenitic. Fox, U.S. Pat. No. 7,240,677 set the transition temperature of the implant and the resistive current heating level so that this elevated temperature implant was below the heat level of tissue injury. This invention is further illustrated in the BioMedical Enterprises, Inc., BME_OSStaple_sell_sheet_B. Flot, U.S. Pat. Nos. 6,323,461 and 6,268,589 used electrical current to heat the staple but had no ability to control the extent of staple shape change.

Though Fox's, U.S. Pat. No. 7,240,677 elevated temperature staple heating strategies have seen extensive clinical use, this style and the body temperature heated implants are deficient due to variation in bone fixation force due to environmental heating or cooling and are soft in their mechanical properties during implantation. These issues and the requirement to have dry ice or an electrical bipolar heating unit have limited the clinical adoption of elevated temperature staples.

The embodiments of the subject invention of this patent overcomes the deficiencies of the memory staples such as 1) requiring heating or cooling, 2) having a temperature dependent fixation force, 3) requiring ancillary equipment to manipulate the implant, 4) being implanted in the soft martensitic phase, 5) requiring an expensive multiple step manufacturing process to set both the staple shape and transition temperatures, and 6) others that become more clear in the review of the embodiments of the subject invention.

Elastic Staples

Mohr, U.S. Pat. No. 3,939,828 first introduced the use of elastic properties of stainless steel for a bone staple. This invention the Osteoclasp™ was an S-shaped bridge staple with convergent legs. (A staple has a "convergent" shape when the legs of the staple are in a convergent orientation, as opposed to a substantially parallel orientation or a divergent orientation). In use, one leg was placed in an angled drill hole and the other pulled with a hook until it could be inserted in a second drill hole. The elastic spring-back of the stainless steel pulled the bone together and caused bone-to-bone compression. The legs are not manipulated to converge and compress, though Mohr's angled drill holes impede staple extrusion from bone. The clinical use of the Mohr staple has been long discontinued due to difficulty in stretching the bridge during placement and the frequency of having the staple unexpectedly released from the hook and spring from the surgical field.

Allen, in U.S. Pat. Nos. 6,348,054, 6,059,787 and 6,783,531 used a bowed bridge shaped staple and a complex instrument to pull the legs of the staple apart to straighten the bowed bridge while impacting the staple legs into bone. The elastic spring back of the bowed bridge staple pulled the bone together and caused bone-to-bone compression. Allen does not manipulate the legs and thus the parallel legs do not converge and resist extrusion from the bony drill holes. The cost of the instrument is high and no commercial embodiment of this invention is known.

Jervis, in U.S. Pat. Nos. 5,067,957 and 4,665,906 introduced the use of nitinol formulated to fully transition from stress induced martensite to austenite at body temperature for the fabrication of bone staples, plates and rods. Monassevitch, in U.S. Pat. No. 6,685,708 teaches the use of pliers or forceps on nitinol staples to plastically change the distance between the legs and allow the martensitic to austenitic crystalline structure of nitinol to move the legs back to the original distance once released. This invention requires the surgeon to change the shape of the staple during implantation, has high fixation force variation and does not provide a feature to impact the staple into bone. The shape recovery causes the staple bridge to shorten but does not angle the legs to resist extrusion from the bony drill holes. Monassevitch, claims a hand operated instrument for manipulating the staple and teaches that the staple must be cold and in its soft martensitic state so that the hand operated instrument has enough force to deform the staple. This is a sufficient deficiency because, the hand deforming is not precise, the staple must be sterile and made cold before deforming and the implant is soft when implanted and thus may bend with the impaction of placement in bone.

Memometal, Inc. sells an elastic staple, the EasyClip™. The EasyClip™ has a straight bridge and convergent legs. Pliers are used to pry the legs apart so that they can be inserted in predrilled holes. When the pliers release the staple legs they can swing in if the drill holes are loose or the bone is soft. The EasyClip™ cannot pull together and compress bone because the bridge is straight and constrained in the drill holes. This straight and rigid bridge defeats compression. The inward movement of the legs only tightens the legs in the holes to impede extrusion of the staple from the bone holes.

The simultaneous requirement for the surgeon to open the staple legs and insert the implant into bone is surgically difficult in many procedures, and for the other reasons noted above, have limited the clinical use of this implant. Memometal, Inc.'s Easy Clip Brochure further illustrates the deficiencies of these staple implants that are elastic and manipulated with pliers, complex instruments, forceps and hooks for stretching. The Easy Clip is described as having super elastic properties and there is no indication that the opening of the legs with pliers creates stress induced martensite in the staple to leg corners and certainly not in the straight bridge.

Though Jervis describes staples and many other medical implant applications the geometry of the staple is not described. Monassevitch presents a Z-shaped bridge that can be compressed into an S-shape but teaches away from legs angled in relation to the bridge and promotes a non-shape changing leg to bridge corner. The Easy Clip has a straight bridge and though its legs can deflect inwards to tighten in the hole this device cannot pull together and compress. This prior art stress induced martensite or super elastic implants have not taken advantage of the geometric leverage provided by the O-shaped or S-shaped bridge at contracting or lengthening or the bridge to leg corner to enhance the amount the staple can pull together and compress two structures. The prior art teaches elastic behavior but teach away from a staple geometry that creates optimal shape change and compression. Consequently, in use these implants have significant disadvantages compared to the embodiments of the subject invention.

The embodiments of the subject invention of this patent overcomes the deficiencies of the prior elastic staples such as 1) requiring the surgeon to stretch the staple to place it in bone, 2) designs that cannot contract their bridge, 3) requiring expensive ancillary equipment such as staple guns to manipulate the implant, 4) requiring the surgeon to change the staple shape with pliers, forceps or other hand operated instruments, 5) cooling of the implant prior to opening for placement, 6) designs that can not simultaneously provide in their bridge and legs geometric leverage to pull together and compress bone, and 6) others deficiencies that will become more clear in the review of the embodiments of the subject invention.

Instrument and Staple Implant Devices and Methods

Shapiro, U.S. Pat. No. 4,414,967 describes a pneumatic staple gun that combined with a staple cartridge violently impacted staples into bone. The staple's legs were divergent so that they pull bone together when inserted. (A staple has a "divergent" shape when the legs of the staple are in a divergent orientation, as opposed to a substantially parallel orientation or a conversion orientation). This implant did not change shape to pull together and compress bone. The instrument was complex, expensive and in aged porous bone sometimes caused bone fracture during staple insertion.

Assell, U.S. Pat. No. 4,527,726 and Bent, U.S. Pat. No. 4,540,110, as did Shapiro U.S. Pat. No. 4,414,967, both illustrated an automatic stapler that forces a staple down a channel with significant energy to impact this implant into bone. These staples do not store mechanical energy or change shape and thus the staples of his system cannot pull together and compress bone. The convenience of these systems is overcome by the high cost, complicated design of the staple gun, and difficulty in cleaning and sterilizing the stapler for repeated patient use.

McHarrie, U.S. Pat. No. 4,415,111 proposed a locator tube having a staple in a slot and a cooperating punch to push the staple from the tube into bone. McHarrie's invention cannot be used with shape changing staples because it does not constrain the staple legs from swinging in or the bridge from shortening. Consequently, the staples of this system do not change shape to pull together and compress bone. Pratt, U.S. Pat. No. 4,438,769, used a simple system to hold the staple bridge in a grasping driver that used a threaded coupler to lock the staple. This system supported the staple during hammer insertion into bone and through its geometry may urge bone together. The staple did not change shape to pull together and compress bone because the system required rigid staples to withstand the bone impaction forces.

The foregoing discussion illustrates the deficiencies of the prior art and the lack of a simple shape changing staple, instrument for its implantation and method of use consistent with the demands of surgery. In the discussion of the embodiments of the subject invention its benefits will be realized as a simple, reliable, low cost solution to present an elastic energy storing shape changing staple to bone and releasing the staple so that it can pull together and compress bone even in the presence of gaps that can form during bone healing.

SUMMARY OF THE INVENTION

The embodiments of the subject invention describe an improved bone staple that stores recoverable mechanical energy in its structure and changes shape to pull together and compress the bone fixation interface. This implant, instrument and method have multiple advantages over prior staples: 1) shape change and compression forces are temperature independent, 2) the staple does not require heat or cooling to activate it, 3) the staple does not need to be stretched or mechanically manipulated by the surgeon to facilitate implantation, 4) the surgeon's sole required effort, pushing the staple into bone, automatically controls the staple's mechanism of shape change and compression, 5) the staple load transfer to bone can be controlled by the surgeon and instrument to minimize the chance of implant induced fracture and 6) the staple bone fixation load is at a maximum and constant during the operative procedure.

Furthermore, a method of manufacturing has been developed that allows the implant to be cut from a rod of material in its closed first shape and then deformed to its as implanted open second shape. This has the cost and time advantage over the current methods of bending shape changing staples from wire and performing heat treatments to set shapes and transition temperatures.

The manufacturing method of the embodiments of the subject invention does not bend so does not impart stress concentrations to the staple. These stress concentration in the prior art staple weaken the corners and bridge, which can result in breakage. The three dimensional cutting methods used for the embodiments of the subject invention do not create stress concentrations and results in a tougher staple.

The manufacturing technique further works with nitinol in its strong austenitic state while the body temperature and electrically heated nitinol staples are in the cold mechanically weak and soft martensitic state. Use of this soft form of nitinol requires drill holes to avoid bending during insertion. The austenitic form used for the embodiments of the subject invention is harder and stronger and can be impacted into bone without concern for deformation that is a distinct advantage over the prior art.

The staple embodiments of the subject invention, since not controlled with heat, are restrained in its open second shape by the extrusion block into which it is inserted. This staple-containing cartridge is combined with a reusable or disposable extrusion instrument for pushing the staple through the cartridge and into bone. This extrusion instrument can be separate or an integral part of the staple cartridge. This allows the use of shape changing staples in reusable and disposable instruments in procedures and under conditions in which the prior art staples cannot be used.

In general, in one aspect, the invention features a staple that includes a staple bridge. The staple bridge includes a shape memory metal. The staple bridge has a bridge-shape such that the bridge can move between a first shape and a second shape with no substantial plastic deformation of the staple bridge. The bridge shape is an S-shaped staple bridge shape or an O-shaped staple bridge shape. The staple further includes a plurality of staple legs adjoined to the staple bridge. The plurality of staple legs include the shape memory metal. The staple is operable for moving between a non-parallel shape and a parallel shape without substantial plastic deformation of the staple. The staple is in the non-parallel shape when the staple bridge is in the first shape and the staple legs are not substantially parallel. The staple is in the parallel shape when the staple is in the second shape and the staple legs are substantial parallel. The staple is operable for storing mechanical energy when the staple in the parallel shape. The staple is operable for moving substantially to the non-parallel shape when the stored mechanical energy is released without a change in temperature of the staple.

Implementations of the invention can include one or more of the following features:

The staple can be operable for use in a medical procedure.

The staple can be a bone staple.

The first shape can be a contracted shape of the staple bridge, and the second shape can be an elongated shape of the staple bridge.

The staple-bridge can have an S-shaped staple bridge shape.

The staple-bridge can have an O-shaped staple bridge shape.

The non-parallel shape can be a convergent shape. The staple legs can be convergent.

The non-parallel shape can be a divergent shape. The staple legs can be divergent.

When the staple are in the parallel shape, the stored mechanical energy of the staple can be predominately stored where the plurality of staple legs are adjoined to the staple bridge and in the curvature of the staple bridge.

The staple can be operable for pulling together and compressing bone when the staple moves from the parallel shape to the non-parallel shape.

The staple can be operable for pulling apart and placing bone under tension when the staple moves from the parallel shape to the non-parallel shape.

The shape memory metal can include nitinol.

The shape memory metal of the staple in the non-parallel shape can be in the austenite form.

The shape memory metal of the staple in the parallel shape can include shape memory metal in the form of stress induced martensite.

The shape memory material can have a material strength such that the staple is operable for implanting in bone without pre-drilling holes in bone.

Each of the staple legs can have a rounded leg tip.

The staple can be a sterilized staple.

In general, in another aspect, the invention features a staple that includes a staple bridge. The staple bridge includes a first super elastic metal. The staple bridge has a bridge-shape such that the bridge can move between a first shape and a second shape with no substantial plastic deformation of the staple bridge. The staple further includes a plurality of staple legs connected to the staple bridge. The plurality of staple legs includes a second super elastic metal. The staple is operable for moving between a non-parallel shape and a parallel shape without substantial plastic deformation of the staple. The staple is in the non-parallel shape when the staple bridge is in the first shape and the staple legs are not substantially parallel. The staple is in the parallel shape when the staple bridge is in the second shape and the staple legs are substantially parallel. The staple has stored mechanical energy when the staple in the parallel shape. The staple is operable for moving substantially to the non-parallel shape when the stored mechanical energy is released without a change in temperature of the staple.

Implementations of the invention can include one or more of the following features:

The first super elastic material and the second super elastic material can be the same material.

The first super elastic material can be able to withstand a strain up to around 6% with no substantial plastic deformation.

The first super elastic material can be able to withstand a strain up to around 8% with no substantial plastic deformation.

The first super elastic material can be able to withstand a strain up to around 13% with no substantial plastic deformation.

The first super elastic material can be able to withstand a strain up to between around 6% and around 13% with no substantial plastic deformation.

The first super elastic material coupled with the design shape of the staple bridge can interact such that the staple bridge can be able to withstand a strain up to around 30% with no substantial plastic deformation.

The non-parallel shape can be a convergent shape. The staple legs can be convergent.

The non-parallel shape can be a divergent shape. The staple legs can be divergent.

The second super elastic material has a material strength such that the staple can be operable for implanting in without pre-drilling holes in bone.

In general, in another aspect, the invention features a staple device that includes a staple. The staple is operable from moving between a parallel shape and a non-parallel shape. The staple device further includes a cartridge. The cartridge has a channel in which a staple can be retained in the cartridge in the parallel shape under strain. The strain of the staple retained in the cartridge is operable for storing mechanical energy in the staple. The cartridge has an opening through which the staple can be extruded from the cartridge. The staple device further includes an extrusion instrument that coupled to the cartridge. The extrusion instrument is operable for extruding the staple from the cartridge through the opening. The staple is operable for spontaneously moving from the parallel shape towards to the non-parallel shape when released from the cartridge. The spontaneous moving of the staple is operable to release at least some of the mechanical energy stored in the staple.

Implementations of the invention can include one or more of the following features:

The staple can include a staple bridge. The staple bridge can have a bridge-shape such that the bridge can move between a first shape and a second shape with non-plastic deformation of the staple bridge. The staple can further include a plurality of staple legs adjoined to the staple bridge. The staple is operable for moving from the parallel shape toward the non-parallel shape due to non-plastic deformation of the staple. The staple is in the non-parallel shape when the staple bridge is in the first shape and the staple legs are not substantially parallel. The staple is in the parallel shape when the staple bridge is in the second shape and the staple legs are substantially parallel.

The staple bridge can have a bridge-shape such that the bridge can move between the first shape and the second shape with substantially no plastic deformation of the staple bridge. The staple can be operable for moving between the parallel shape and the non-parallel shape with substantially no plastic deformation of the staple.

The channel can have a shape for holding the staple in the parallel shape.

The channel can have a shape that can receive the staple when the staple is in the parallel shape.

The channel can have a first portion shape having a shape that can receive the staple when the staple is in the non-parallel shape and a second portion that has contours operable for changing the shape of the staple from the non-parallel shape to the parallel shape.

The non-parallel shape can be a convergent shape. The staple legs can be convergent.

The non-parallel shape can be a convergent shape, and the staple legs can be convergent. The staple-bridge can have an S-shaped staple bridge shape. The channel can be shaped to retain the bridge shape in an elongated form.

The non-parallel shape can be a convergent shape, and the staple legs can be convergent. The staple-bridge can have an O-shaped staple bridge shape. The channel can be shaped to retain the bridge shape in an elongated form.

The non-parallel shape can be a divergent shape. The staple legs can be divergent.

The non-parallel shape can be a divergent shape, and the staple legs can be divergent. The staple-bridge can have an S-shaped staple bridge shape. The channel can be shaped to retain the bridge shape in a contracted form.

The non-parallel shape can be a divergent shape, and the staple legs can be divergent. The staple-bridge can have an O-shaped staple bridge shape. The channel can be shaped to retain the bridge shape in a contracted form.

The staple can be operable for use in a medical procedure.

The staple can be a bone staple.

The cartridge can further include a retention tab operable for holding the staple in the channel. The cartridge can further include a cam operably connected to the retention tab. The cam can be operable for releasing the retention tab when the extruder is used to extrude the staple from the cartridge.

The staple can include a metal that includes stainless steel, titanium, nitinol, one of their alloys, or a combination thereof.

The staple can include a shape memory metal.

The staple can include nitinol.

The staple can be operable for spontaneously moving from the parallel shape to substantially the non-parallel shape when released from the cartridge.

The staple can include a super elastic metal.

The staple can not change shape due to a change in temperature of the staple.

The extrusion instrument can be operable for providing a force capable of advancing the staple from the cartridge and into bone.

The cartridge can be a sterilized cartridge.

The cartridge can be disposable.

The extrusion instrument can be an integral disposable extrusion instrument.

The extrusion instrument can be permanently attached to the cartridge.

The extrusion instrument can be a reusable extrusion instrument that is detachable from the cartridge.

The extrusion instrument can have an extrusion mandrel that has a shape that matches the second shape of the staple bridge.

The cartridge can further include a retention tab operable for holding the staple in the channel. The extrusion mandrel can be operable for disengaging the tab when extruding the staple from the cartridge.

The cartridge can include sterilizable material.

The sterilizable material can be plastic, ceramic, metal, or a combination thereof.

The sterilizable material can be a material that would not be substantially damaged following a multitude of sterilization cycles.

In general, in another aspect, the invention features a method that includes forming a staple in a non-parallel shape. The method further includes applying mechanical energy to the staple to move the staple to a parallel shape. During this step, at least some of the mechanical energy is stored in the staple due to elastic deformation of the staple. The method further includes positioning the staple in a cartridge. The method further includes maintaining the staple in the parallel shape within the cartridge. The mechanical energy is operable for moving the staple substantially toward the non-parallel shape when the staple is extruded from the cartridge.

Implementations of the invention can include one or more of the following features:

The movement of the staple to the parallel shape can not substantially plastically deform the staple.

The mechanical energy can be operable for moving the staple substantially to the non-parallel position when the staple is extruded from the cartridge.

The staple can be operable for use in a medical procedure.

The staple can be a bone staple.

The step of applying mechanical energy can occur before the step of positioning the staple in the cartridge.

The step of applying mechanical energy can occur while performing the step of positioning the staple in the cartridge.

The step of forming the staple can include cutting the staple into the first shape.

The staple can be cut from a rod of material.

The staple can be cut using a three-dimensional cutting technique.

The inline cutting technique can be a milling technique, an electro-discharge technique, a water jet technique, a laser machining technique, and a combination thereof.

The staple can be formed from a metal that is stainless steel, titanium, nitinol, one of their alloys, or a combination thereof.

The staple can be formed from a shape memory metal.

The staple can be formed from nitinol.

The staple can be formed from a super elastic metal.

The non-parallel shape can be a convergent shape.

The non-parallel shape can be a divergent shape.

The staple can include a staple bridged adjoined to a plurality of staple legs.

The non-parallel shape can be a convergent shape. The staple bridge can be contracted, and the staple legs can be convergent when the staple is in the non-parallel position.

The staple bridge can be elongated and the staple legs are substantially parallel when the staple is in the parallel position.

The step of applying mechanical energy to the staple can include elongating the staple bridge.

The step of applying mechanical energy to the staple can include moving the staple legs from a convergent orientation to a substantially parallel orientation.

The non-parallel shape is a divergent shape. The staple bridge can be elongated, and the staple legs can be divergent when the staple is in the non-parallel position. The staple bridge can be contracted and the staple legs are substantially parallel when the staple is in the parallel position.

The step of applying mechanical energy to the staple can include contracting the staple bridge.

The step of applying mechanical energy to the staple can include moving the staple legs from a divergent orientation to a substantially parallel orientation.

The staple-bridge can have an S-shaped staple bridge shape.

The staple-bridge can have an O-shaped staple bridge shape.

The step of forming the staple can include forming the staple from a shape memory metal in austenite form. The step of applying mechanical energy to the staple can include forming stress induced martensite in the staple.

The staple can include a staple bridged adjoined to a plurality of staple legs with each of the plurality of staple legs adjoined to the staple bridge at corners. The step of applying mechanical energy to the staple can include forming stress induced martensite in the staple at a site selected from the group consisting of the staple bridge and the corners.

The step of positioning the staple in the cartridge can include positioning the staple in a channel that maintains the staple in the parallel shape.

The staple can include an S-shaped staple bridge. The channel can have a shape to maintain the staple having an elongated S-shaped staple bridge.

The staple can include an O-shaped staple bridge. The channel can have a shape to maintain the staple having an elongated O-shaped staple bridge.

The staple can include an S-shaped staple bridge. The channel can have a shape to maintain the staple having a contracted S-shaped staple bridge.

The staple can include an O-shaped staple bridge. The channel can have a shape to maintain the staple having a contracted O-shaped staple bridge.

The method can further include sterilizing the cartridge and the staple.

The method can further include extruding the staple from the cartridge into bone.

In general, in another aspect, the invention features

Implementations of the invention can include one or more of the following features:

In general, in another aspect, the invention features a method that includes positioning a cartridge that includes a bone staple over a first bone structure and a second bone structure. The bone staple includes a plurality of staple legs adjoined to a staple bridge. The bone staple is being held in a parallel shape under strain by the cartridge. The method further includes extruding the bone staple from the cartridge into the first bone structure and the second bone structure. The bone staple spontaneously moves toward a non-parallel shape after extrusion from the cartridge.

Implementations of the invention can include one or more of the following features:

The bone staple can be used for musculoskeletal surgical repair of the bone structures.

The method can further include bringing the first bone structure and the second bone structure together such that the first bone structure and the second bone structure are contiguous. The method can further include inserting a first staple leg of the plurality of the staple legs of the bone staple into the first bone structure and a second staple leg of the plurality of the staple legs of the bone staple into the second bone structure before completely extruding the bone staple from the cartridge. The method can further include pushing the first staple leg into the first bone structure and the second staple leg into the second bone structure during the step of extruding the bone staple from the cartridge.

The method can further include drilling a first hole in the first bone structure before inserting the first staple leg into the first bone structure. The method can further include drilling a second hole in the second bone structure before inserting the second staple leg into the second bone structure.

The first staple leg can be inserted into an undrilled portion of the first bone structure. The second staple leg can be inserted into an undrilled portion of the second bone structure.

The staple bridge can be operable to deform when moved between a first shape and a second shape. The deformation of the staple bridge can include non-plastic deformation of the staple bridge when moved between a first shape and a second shape. The bone staple can be in the non-parallel shape when the staple bridge is in the first shape. The bone staple can be in the parallel shape when the staple bridge is in the second shape. The bone staple can be operable to deform when moved between the non-parallel shape and the parallel shape. The deformation of the bone staple can include non-plastic deformation of the bone staple when moved between the non-parallel shape and the parallel shape.

The deformation of the staple bridge can further include plastic deformation of the staple bridge when moved between the first shape and the second shape. The deformation of the bone staple can further include plastic deformation of the bone staple when moved between the non-parallel shape and the parallel shape.

The deformation of the staple bridge can include non-plastic deformation of the staple bridge without substantial plastic deformation of the staple bridge when moved between a first shape and a second shape. The deformation of the bone staple can include non-plastic deformation of the bone staple without substantial plastic deformation when moved between the non-parallel shape and the parallel shape.

The deformation of the staple bridge can include elastic deformation of the staple bridge when moved between the first shape and the second shape. The deformation of the bone staple can include elastic deformation of the staple bridge when moved between the non-parallel shape and the parallel shape.

The deformation of the staple bridge can include pseudo elastic deformation of the staple bridge when moved between the first shape and the second shape. The deformation of the bone staple can include pseudo elastic deformation of the staple bridge when moved between the non-parallel shape and the parallel shape.

The bone staple can include a metal that is stainless steel, titanium, nitinol, one of their alloys, or a combination thereof.

The bone staple can include a shape memory metal.

The bone staple can include nitinol.

The bone staple can include a super elastic metal.

The staple bridge can have an S-shaped staple bridge shape. The channel can be shaped to retain a bone staple having a staple bridge having an elongated S-shaped staple bridge.

The staple-bridge can have an O-shaped staple bridge shape. The channel can be shaped to retain a bone staple having a staple bridge having an elongated O-shaped staple bridge.

The bone staple can be operable not to change shape due to a change in temperature.

An extrusion instrument can be used to extrude the bone staple from the cartridge and into first bone structure and the second bone structure.

The cartridge can include a retention tab operable for holding the bone staple in the channel. The extrusion instrument can disengage the tab when extruding the bone staple from the cartridge.

The non-parallel shape can be a convergent shape. The staple legs can be convergent.

The non-parallel shape can be a divergent shape. The staple legs can be divergent.

In general, in another aspect, the invention features a method for surgically repairing bone structures that includes selecting a first cartridge including a first bone staple in which the first bone staple is being held in a first parallel shape under strain by the first cartridge. The method further includes positioning the cartridge over a first portion of the bone structures. The method further includes extruding the first bone staple from the first cartridge into the first portion of the bone structures, wherein the first bone staple spontaneously moves toward a first non-parallel shape after extrusion from the first cartridge. The method further includes selecting a second cartridge including a second bone staple in which the second bone staple is being held in a second parallel shape under strain by the second cartridge. The method further includes positioning the second cartridge over a second portion of the bone structures. The method further includes extruding the second bone staple from the second cartridge into the second portion of the bone structures, wherein the second bone staple spontaneously moves toward a second non-parallel shape after extrusion from the second cartridge.

Implementations of the invention can include one or more of the following features:

The first bone staple and the second bone staple can be the same type of bone staples.

The first parallel shape can be the same as the second parallel shape. The first non-parallel shape can be the same as the second non-parallel shape.

The first bone staple and the second bone staple can be different types of bone staples.

The difference between first bone staple and the second bone staple can be bone staple size, bone staple material, bone staple shape, number of bone staple legs, shape of the bone staples, parallel shapes of the bone staple, non-parallel shapes of the bone staple, staple bridges of the bone staples, or a combination thereof.

The first parallel shape and the second parallel shape can be different. The first non-parallel shape and the second non-parallel shape can be different.

The first non-parallel shape can be a first convergent shape. The second non-parallel shape can be a second convergent shape. The first non-parallel shape and the second non-parallel shape can be the same shape or different shapes.

The first bone non-parallel shape can be a first divergent shape. The second non-parallel shape can be a second non-parallel shape. The first non-parallel shape and the second non-parallel shape can be the same shape or different shapes.

The first non-parallel shape can be a convergent shape. The second non-parallel shape can be a divergent shape.

REFERENCE NUMERALS

Figure 1A:
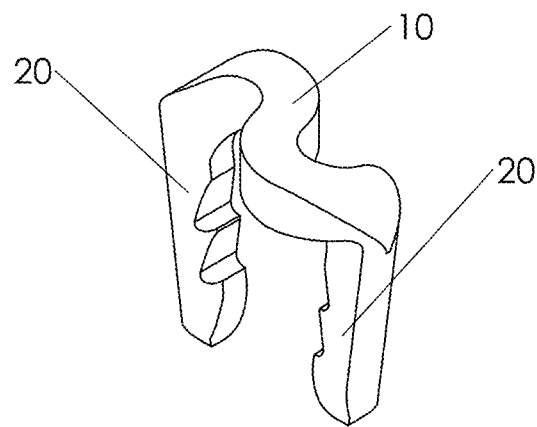
FIG. 1A: S-shaped bridge 10 staple as cut from a rod of material in a closed first shape having a contracted bridge and convergent legs 20, orthogonal view.

10 S-shaped staple bridge in a first closed shape.
12 S-shaped staple bridge in a second open shape.
20 S-shaped staple legs in the first closed shape.
22 S-shaped staple legs in the second open shape.
30 S-shaped staple tip of leg.
40 Bone retention notches (barbs).
50 Corner of staple leg 20 to bridge 10.
60 O-shaped staple bridge in a contracted first closed shape.
62 O-shaped staple legs inwardly converging in a first closed shape.
70 O-shaped staple bridge in an elongated second open shape.
80 O-shaped staple legs parallel in a second open shape.
90 S-shaped staple cartridge.
92 S-shaped staple extrusion channel.
94 S-shaped staple retention tab to retain the staple.
96 S-shaped staple cam to release the staple.
98 O-shaped staple retention tab to retain the staple.
100 O-shaped staple cartridge.
102 O-shaped staple extrusion channel.
104 O-shaped staple retention tab to retain the staple.
106 O-shaped staple cam to release the staple.
110 Reusable staple extrusion instrument handle.
112 Reusable S-shaped staple extrusion mandrel.
114 Extrusion mandrel staple cartridge retention tab lock slot.
120 Integral single use staple extrusion instrument handle.
130 Force vs. temperature for the staple embodiments of the subject invention.
132 Force vs. temperature for a body temperature nitinol staple.
134 Force vs. temperature for the electrical heated nitinol staple during cooling.
136 Force vs. temperature for the electrical heated staple during heating.
140 Force versus percent shape recovery curve.
142 Staple in a second open shape with no recovery and maximum bone fixation force.
144 Staple in a first closed shape with full shape recovery associated with no bone fixation force.
150 Stress vs. strain curve of materials, such as stainless steel, suitable for embodiments of the subject invention that exhibit linear elastic behavior.
152 Linear elastic region of the stress vs. strain curve.
154 Plastic deformation region of the stress vs. strain curve.
160 Nitinol stress vs. strain curve.
162 Upper plateau stress of nitinol exhibited as the staple is deformed at room temperature from a first closed to a second open shape (which includes pseudo elastic deformation).
164 Upper plateau stress of nitinol exhibited as the staple is deformed while cold (below martensitic finish temperature) from a first closed to a second open shape.
166 Lower plateau stress of nitinol at room temperature which relates to the energy stored in the staple that causes the staple to apply force to bone or transition from a second open to a first closed shape.
168 Stress of nitinol exhibited as the staple is deformed at room temperature from a first closed to a second closed shape in the region where the deformation was primarily elastic (no substantial plastic deformation and little to no substantial pseudo elastic deformation).
169 Stress of nitinol exhibited as the staple is deformed at room temperature where there is substantial plastic deformation of the nitinol.
170 Unrecoverable strain of annealed nitinol.
172 Nitinol stress strain curve with substantially recoverable elastic deformation up to 6% strain and plastic deformation thereafter.

180 Square bar of nitinol or materials, not limited to stainless steel, that exhibit linear elastic behavior.

182 Staple shaped cavity left in the square bar after cutting using three-dimensional cutting techniques.

DETAILED DESCRIPTION

The embodiments of the subject invention consist of a staple with a plurality of legs commonly in a U- or table shaped configuration where the U-shaped has two legs and the table-shaped has 4 legs. All staple styles independent of the number of legs have a bridge that joins the plurality of legs.

As discussed and described herein, embodiments of the present inventions include staples and methods of use including staples in which the staples are able to move between two shapes, with, generally, one shape being a "parallel" shape and the other shape being a "non-parallel" shape. A staple has a "parallel" shape when the legs of the staple are in a substantially parallel orientation, as opposed to a convergent orientation or a divergent orientation. A staple has a "non-parallel" shape when the legs of the staple are not in a substantially parallel orientation, i.e., the staple is in a convergent orientation or a divergent orientation.

When a staple is a "convergent staple," the staple is able to move between a parallel shape (i.e., the legs of the convergent staple are substantially parallel) and a convergent shape (i.e., the legs of the staple are in a convergent orientation). Since the non-parallel configuration of a convergent staple has converging staple legs, the non-parallel shape of a convergent staple is also referred to as the "closed" shape of a convergent staple. Likewise, the parallel shape of a convergent staple is also referred to as the "open" shape of a convergent staple.

When a staple is a "divergent" staple, the staple is able to move between a parallel shape (i.e., the legs of the divergent staple are substantially parallel) and a divergent shape (i.e., the legs of the divergent staple are in a divergent orientation). Since the non-parallel configuration of a divergent staple has diverging staple legs, the non-parallel shape of a convergent staple is also referred to as the "open" shape of a divergent staple. Likewise, the parallel shape of a divergent staple is also referred to as the "closed" shape of a divergent staple.

Whether a staple is in an open shape or a closed shape depends upon the orientation of staple legs and whether the staple is a convergent staple or a divergent staple. The "open" shape of a convergent staple and the "closed" shape of a divergent staple are the circumstances in which the legs of the staple have a substantially parallel orientation. A convergent staple thus moves from its open shape to its closed shape when the legs of the convergent staple move from the substantially parallel orientation to a convergent orientation. The divergent staple thus moves from its closed shape to its open shape when the legs of the divergent staple move the substantially parallel orientation to a divergent orientation.

The staple embodiments of the subject invention are designed to internally store mechanical energy in its structure and expend energy to change the shape of the staple or apply force to bone. Mechanical energy is stored in the metal matrix and is recoverable. Generally, the mechanical energy is stored when the staple embodiments are in a parallel shape (i.e., an open shaped convergent staple or a closed shaped divergent staple), and the mechanical energy is recovered when then the staple embodiments move toward their non-parallel shape (i.e., a closed shaped convergent staple or an open shaped divergent staple.

In metals that exhibit linear elastic deformation the energy is stored as molecular bonds are strained but not broken. Nitinol deformation strains and rearranges molecular bonds to store mechanical energy. This energy is recovered when the metal grossly changes shape as a result of its crystalline structure transitions from martensite to austenite. Though staples with many legs are included in some embodiments of the subject invention the U-shaped staple will be used by example to illustrate but not limit embodiments of the subject invention.

Figure 14:
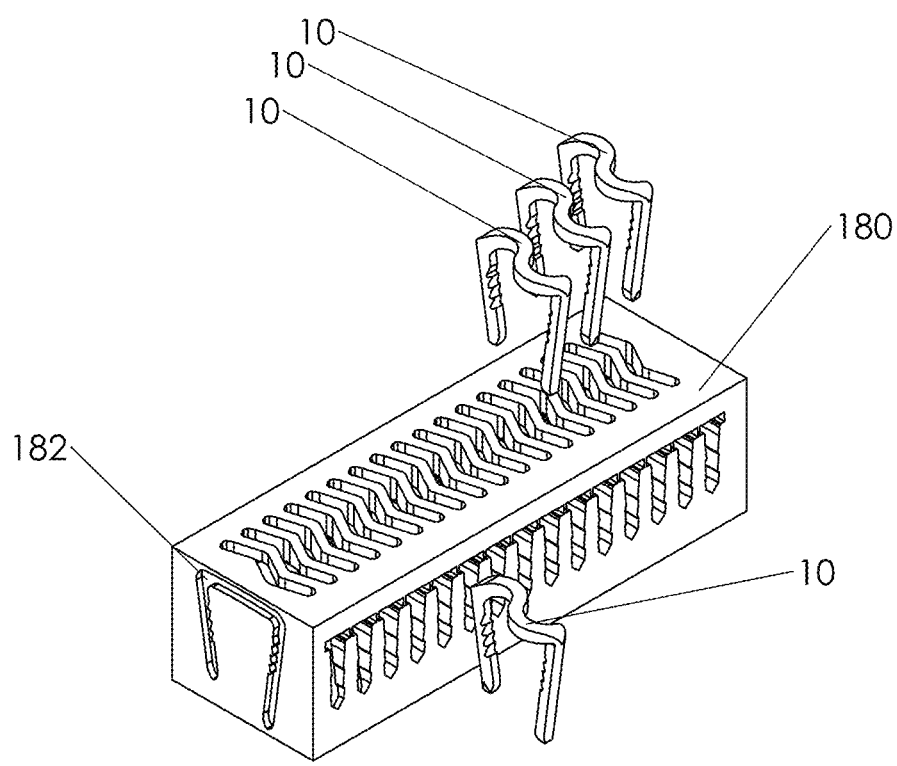
FIG. 14: Shows an illustration of inline cutting manufacturing method that cut, by example, the S-shaped bridge 10 staple, in its closed first shape from a metal bar 180 to leave a staple cavity 182 to produce a staple 10 that requires only straining to an open second shape S-shape bridge 12 staple. In this second open shape the staple is configured for implantation.

The S-shaped staple embodiment of the subject invention in its closed first shape (closed with the bridge 10 contracted and legs 20 deflected together, i.e., the S-shaped staple embodiment is in a convergent shape) is shown in an orthogonal view in FIG. 1A. The staple is cut from a rod 180 of material in this closed first shape using three dimensional cutting techniques such as but not limited to milling, electro-discharge, water jet, or laser machining as shown in FIG. 14.

Figure 1B:
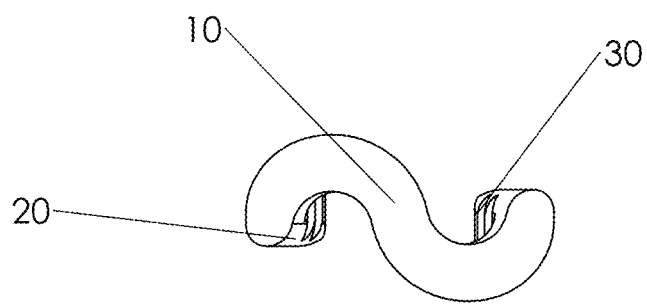
FIG. 1B: S-shaped bridge 10 staple as cut from a rod of material in the closed first shape having a contracted bridge, convergent legs 20 and the leg tip 30, top view.
Figure 1C:
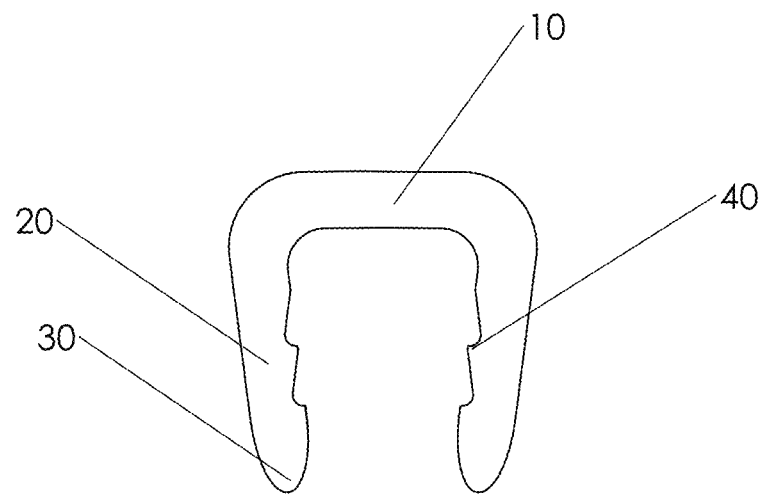
FIG. 1C: S-shaped bridge 10 staple as cut from a rod of material in the closed first shape having a contracted bridge and convergent legs 20, leg tip 30 and barbs 40, front view.

The top view shows the staple bridge 20, legs 20 and leg tip 30, in FIG. 1B. The bridge 10 is undulated and contracted and the legs 20 are angled together in this first closed shape. The leg tips 30 can be seen to converge and can be rounded for insertion into a drill hole or sharp for impaction into bone, FIG. 1C.

Figure 2A:
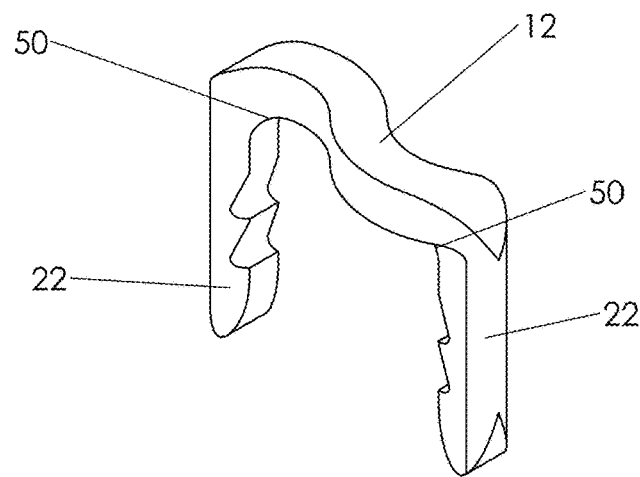
FIG. 2A: S-shaped bridge 12 staple in the open second shape with an elongated bridge 12 and parallel legs 22 that have corners 50 with the bridge 12 in its as implanted condition, orthogonal view.
Figure 2B:
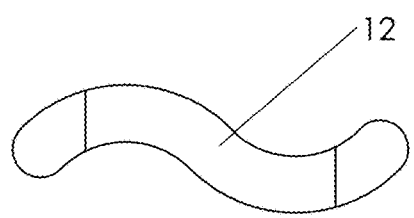
FIG. 2B: S-shaped bridge 12 staple in the open second shape with an elongated bridge 12 in its as implanted condition, top view.
Figure 2C:
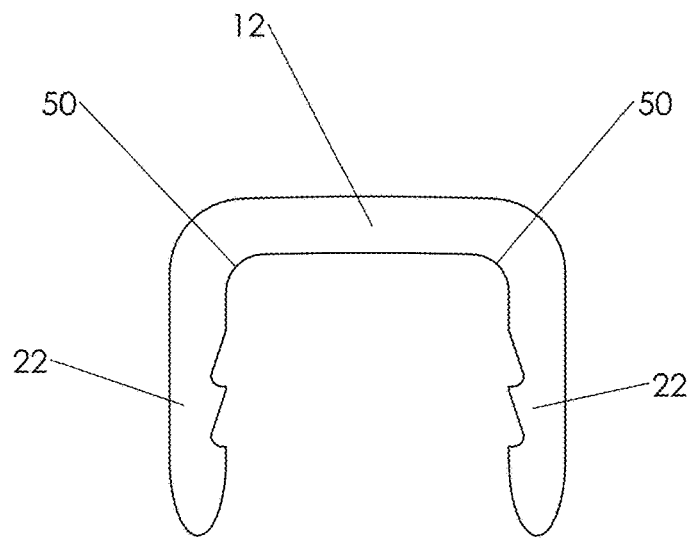
FIG. 2C: S-shaped bridge 12 staple in the open second shape with an elongated bridge 12, parallel legs 22 and corners 50 in its as implanted condition, front view.

The S-shaped staple in an open second shape with parallel legs 22 and extended bridge 12 is in its as implanted configuration: FIGS. 2A-2C. In this open second shape the staple's undulated bridge 12 has been lengthened and the staple legs have been strained, predominantly at the corners 50 adjoining the bridge 12 so that each leg 22 is parallel with one another.

This strain in the bridge 12 and corners 50 stores energy by 1) stretching molecular bonds within their recoverable elastic range and/or by 2) creating recoverable stress induced martensite in its structure if fabricated from a shape memory metal, such as nitinol.

With respect to the former, this linear elastic behavior (caused by the stretching of molecular bonds) is common to spring tempered metals, including, but not limited to, stainless steel, titanium, nickel-chromium alloys (such as Inconel alloys), memory shaped materials (such as nitinol), and other alloys. This is behavior is referred to as "elastic deformation" in that once the strain is removed, the molecules will no longer remained stretched and substantially return to their original position (thus releasing the stored energy).

With respect to the former, this change of structure occurs in certain materials, such as shape memory metals (like nitinol) that can transform from one structure form to another structure form. Shape memory materials, like nitinol, have an austenite phase (cubic B2 structure) and a martensite phase (monoclinic B19' structure). Strain in the bridge 12 and corners 50 can cause stress induced transformation of the shape memory metal such that a portion of the shape metal material (such as in the bridge 12 and the corners 50) will transform from austenite to martensite. This behavior is referred to as "pseudo elastic deformation" in that once the strain is removed, the shape memory material will return to austenite, and the material will substantially return to its original position (thus releasing the stored energy). When pseudo elastic deformation (and elastic deformation) occurs before any substantial conventional plasticity, the shape memory material is referred to as exhibiting "super elasticity."

Over-stretching can lead to formation of permanent deformation that renders the material incapable of returning completely to its original shape (or for reverting to austenite). This behavior is referred to as "plastic deformation" and also "permanent deformation" in that that when the strain is removed the material that is permanently deformed will not substantially return to its original shape. The combined behavior of elastic deformation and pseudo elastic deformation are sometimes referred to collectively as "non-plastic deformation" and "non-permanent deformation."

It should be noted that a material can be plastically deformed in some portions and non-plastically deformed in other portions. Indeed, the non-plastic deformations may itself be a combination of elastic deformations and pseudo-elastic deformations. Thus, a material under strain could deform having a plastic deformation component, a non-plastic deformation component, and a pseudo elastic deformation component. For materials that do not change phase under stress, the pseudo elastic deformation component would basically be zero.

As the amount of non-plastic deformation component increases versus the amount of plastic deformation component, the more the material will tend to move toward its original shape (i.e., return toward its original shape) when the strain is removed.

For instance, when the plastic deformation component is insubstantial (i.e., the material will substantially return to its original shape when the strain is removed), the deformation components are substantially all non-plastic deformation components. In the present application, there is "no substantial plastic deformation" when the material is substantially able to return to its original configuration after the stain is removed (i.e., the plastic deformation component is basically insubstantial when compared to the non-plastic deformation component). In some embodiments of the present invention, the strain in the bridge 12 and corners 50 stores energy with no substantial deformation of the staple 10 (including no substantial deformation of the bridge 12 and corners 50).

Alternatively, for instance, the deformation may include both a substantial plastic deformation component and a substantial non-plastic deformation component. A material could be plastically deformed to a degree that it cannot return to its original shape once the strain is removed; but, the material could still tend to move back toward (but not completely) to its original shape when the strain is removed. Strain in the bridge 12 and corners 50 could store energy due to non-plastic deformation (substantial elastic and/or pseudo elastic deformation) can occur even when there is substantial plastic deformation of the staple. Thus, in some embodiments of the present invention, the strain in the bridge 12 and corners 50 stores energy even when there is substantial deformation of the staple 10 (including substantial deformation of the bridge 12 and/or corners 50). Generally, such materials are not shaped memory metals, but usually other materials that exhibit substantial elastic deformation components even when deformed in conjunction with plastic deformation of the material.

Figure 3A:
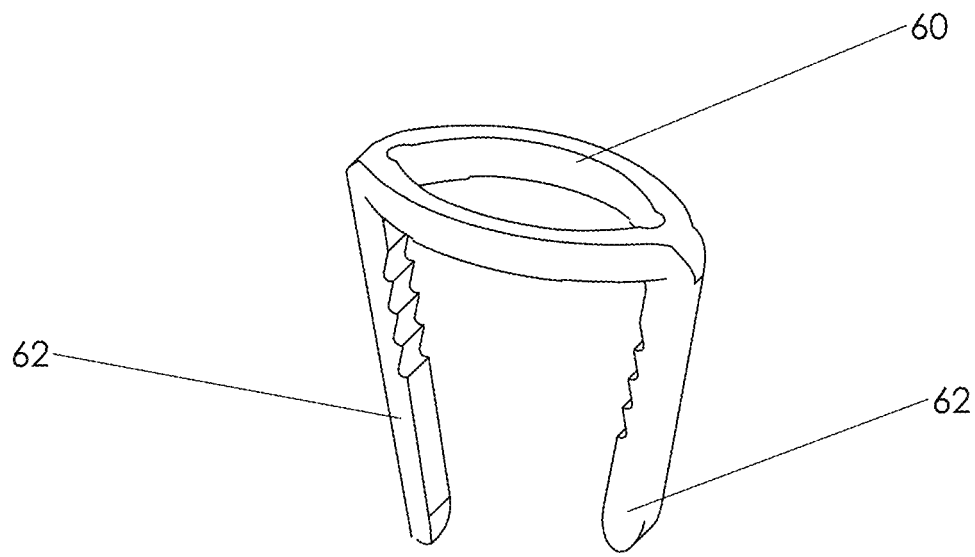
FIG. 3A: Staple with O-shaped bridge 60 in a closed first shape with contracted bridge 60 and converging legs 62, orthogonal view.

Returning to the bridge shape of the staple, an alternate embodiment of the staple (shown in FIGS. 1A-1C and 2A-2B) uses an O-shaped bridge 60 and is shown in a closed first shape in FIG. 3A. The O-shaped dual bridge 60 staple is contracted and the legs 62 are deflected together when cut from a bar.

Figure 3B:
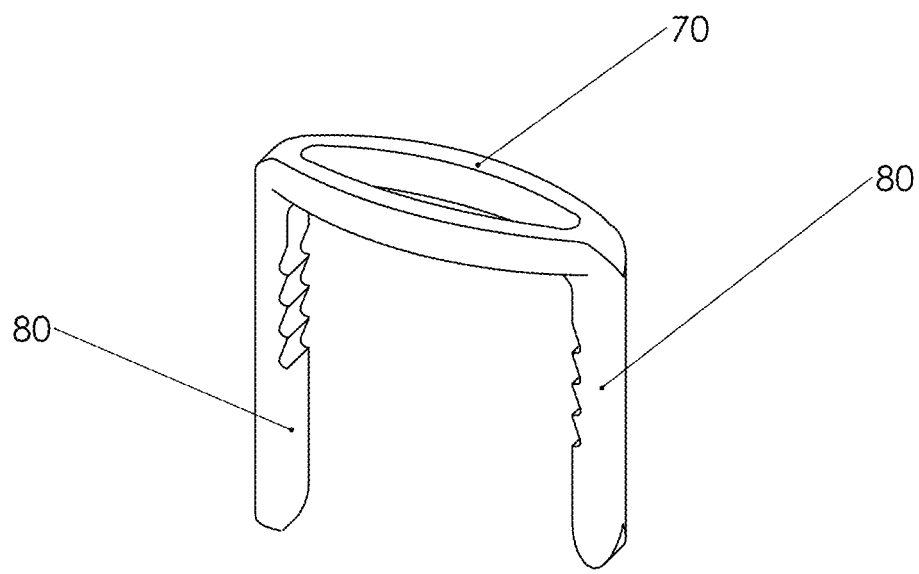
FIG. 3B: Staple with narrowed and elongated O-shaped bridge 70 in an open second shape having parallel legs 80, orthogonal view.

In its second open shape the O-shaped bridge 70 is extended and legs 80 are parallel, FIG. 3B. This is the as implanted shape. When released in bone the stored mechanical energy cause the legs 80 to move towards one another and the bridge 70 to contract to pull together and compress bone.

Prior art, shape changing nitinol staples were cut from wire, bent and heat treated in multiple steps to form a U-shape bridge-to-leg configuration and S-shaped bridge. After these steps the prior art staples are then heat treated a final time to set the transition temperature to match the needs of a body temperature or electrically heated nitinol bone staple.

The manufacturing methods of embodiments of the subject invention for shape changing staples significantly simplifies manufacturing, reduces cost and minimizes staple performance variation over the prior art. Manufacturing of embodiments of the staple requires two steps. Step 1: cut the staple in its closed first shape and Step 2: simultaneously strain the legs 20 to become the parallel legs 22 and the S-shaped bridge 10 to become elongated S-shaped bridge 12. This straining stores mechanical energy in the staple's metal matrix during manufacturing.

This energy stored when the staple is in its second open shape wants to spontaneously return the staple geometry to the first closed shape if released. To maintain the staple in its second open shape during shipping, handling and implantation the subject staple is retained in an extrusion cartridge. The staple is placed in the cartridge during manufacturing.

To place the staple in the cartridge the staple is strained into the second open shape and inserted into the S-shaped or O-shaped extrusion channel. Alternatively the extrusion channel can receive a staple in a first closed shape and when extruded through the cartridge the staple is acted on by features in the cartridge channel that manipulate and strain the staple to a second open shape prior to implantation.

Figure 4:
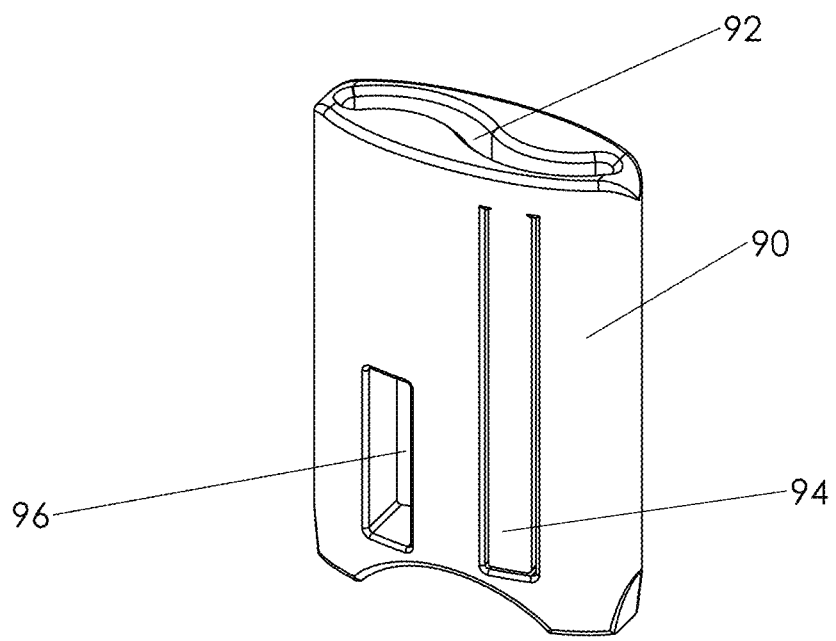
FIG. 4: S-shaped staple extrusion cartridge 90 with undulating s-shaped extrusion channel 92, staple locking tab 94 and staple release cam 96.

The S-shaped staple storage, sterilization, retention and extrusion cartridge 90 is shown in FIG. 4. The cartridge 90 has an internal shape 92 to hold the staple in its second open shape S-shaped bridge 12 staple configuration, a retention tab 94 to hold the staple in the cartridge, and a cam 96 to release the staple when extruded by the staple insertion instrument.

Figure 5:
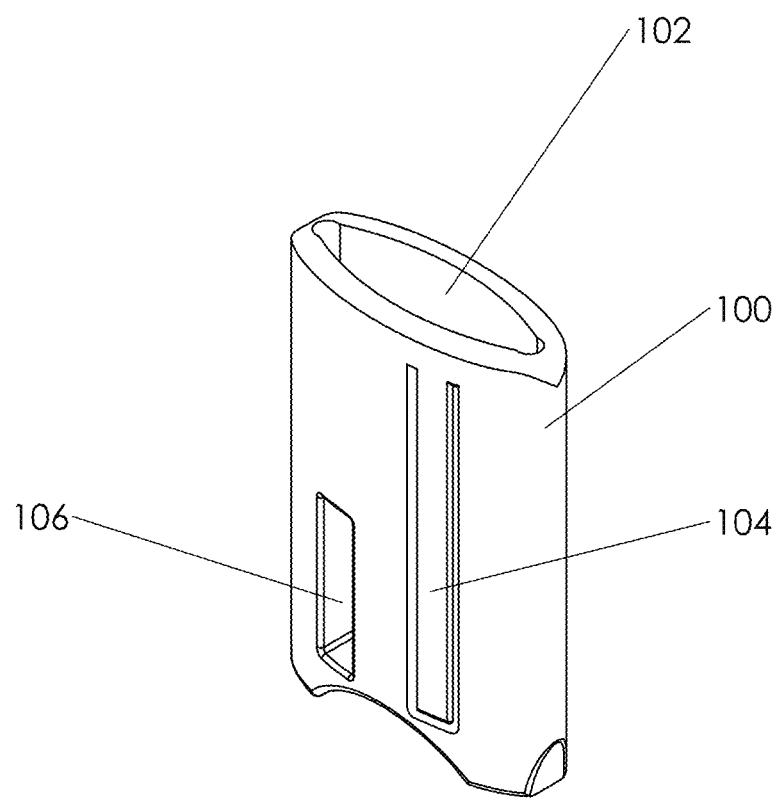
FIG. 5: O-shaped staple extrusion cartridge 100 having an O-shaped extrusion channel 102, staple locking tab 104 and staple capture means 106.

The O-shaped staple storage, sterilization, retention and extrusion cartridge 100 is shown in FIG. 5. The cartridge 100 has an internal shape 102 to hold or cause the staple to strain to its second open shape O-shaped bridge 70 configuration. The cartridge can have a retention tab 104 to retain the staple in the cartridge 100, and a cam 106 to release the staple when extruded by the staple extrusion instrument.

Cartridge retention tabs 94 and 98 and release cams 96 and 106 may not be required for high force staples where wall pressure of the staple against the cartridge channel 92 or 102 is sufficiently high to create friction. This embodiment must create enough staple-to-channel friction so that the extrusion forces are not excessive but the retention of the staple in the cartridge is sufficient.

Figure 6A:
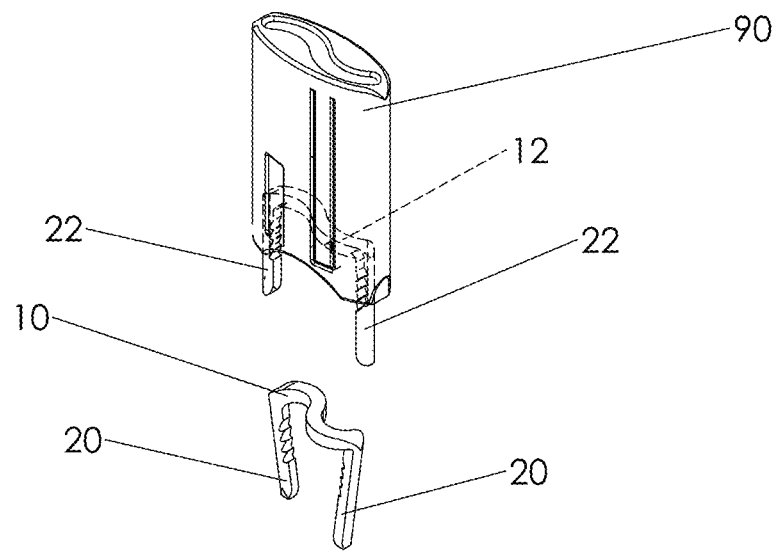
FIG. 6A: Schematic of S-shaped bridge 12 staple in its open second shape with parallel legs 22 illustrated partially within the extrusion cartridge 90 and also shown below in its first closed S-shaped bridge 10 staple configuration with convergent legs 20. This schematic illustrates the retention of the open second S-shaped bridge 12 staple within the cartridge 90 and the return of the staple to a first closed shaped bridge 10 staple when extruded from the cartridge.
Figure 6B:
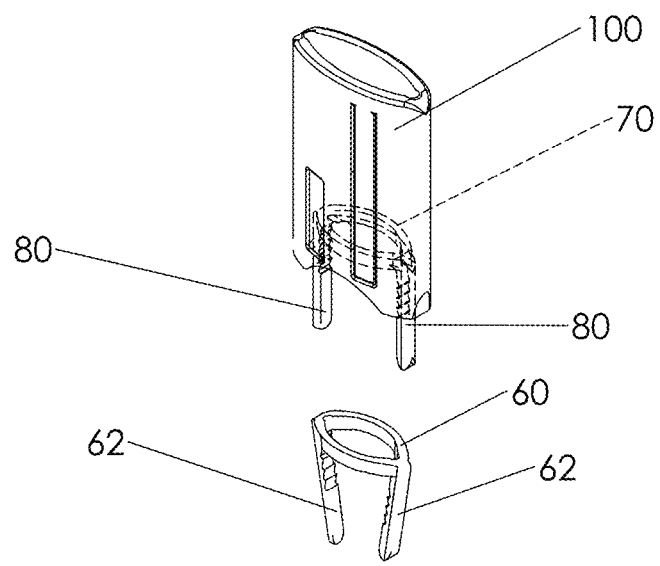
FIG. 6B: Schematic of O-shaped bridge 70 staple in its open second shape with parallel legs 80 illustrated partially within the extrusion cartridge 100 and then shown below in its first closed O-shaped bridge 60 staple configuration having convergent legs 62. This schematic illustrates the retention of the open second bridge shape 70 within the cartridge 100 and the return to a first closed O-shaped bridge 60 staple with convergent legs 62 when extruded from the cartridge.

A schematic of an S-shaped staple in a cartridge 90 with elongated bridge 12 and parallel legs 22 when retained in the cartridge and below after extrusion from the cartridge 90 in its recovered first closed shape with contracted bridge 10 and inward deflected legs 20, FIG. 6A. A schematic of an O-shaped staple shown in the open second shape with elongated bridge 70 and parallel legs 80 while retained within the cartridge 100 and below after extrusion of the O-shaped staple from the cartridge 100 with its bridge 60 contracted and its legs 62 deflected inward, FIG. 6B.

The staple is extruded from the cartridge with a separate reusable extrusion instrument 110 or integral disposable extrusion instrument 120. This allows the clinical product to be part of a hospital sterilized tray or a pre-sterilized fully disposable procedure specific kit.

Figure 7:
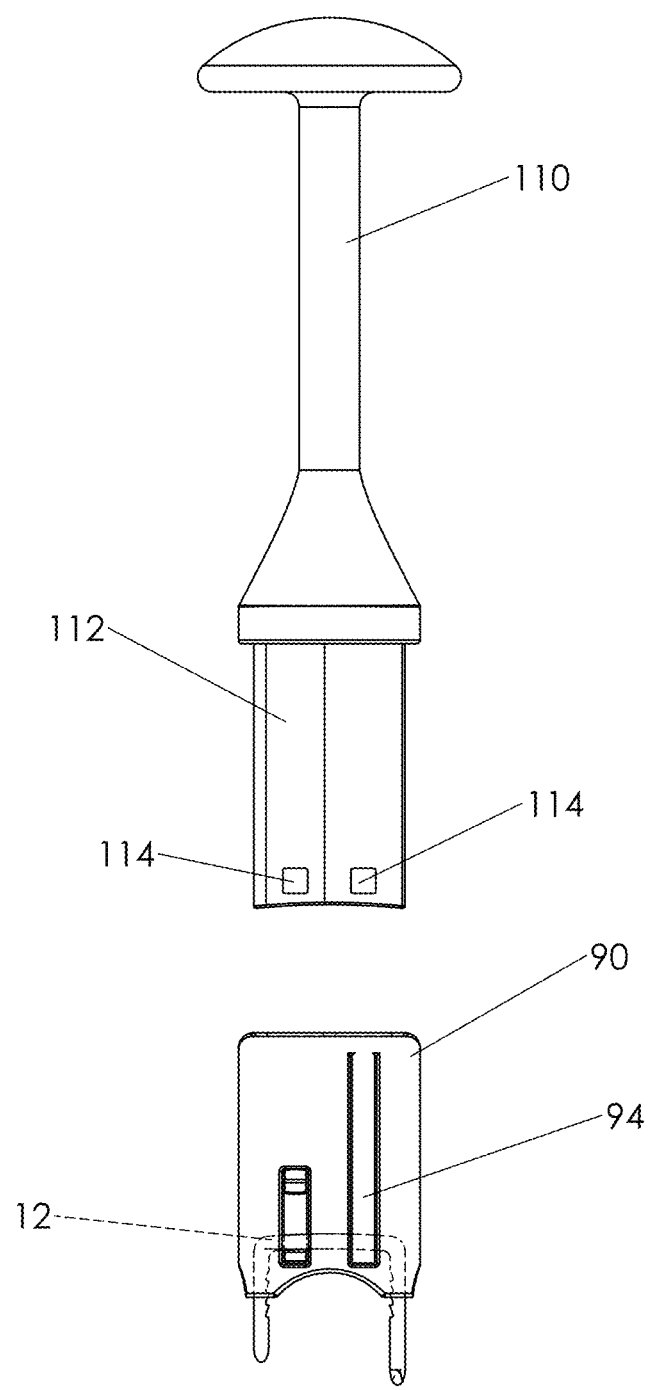
FIG. 7: Reusable staple extrusion instrument 110 with S-shaped extrusion mandrel 112, having temporary locking means 114 shown above its attachable cartridge 90 having temporary locking tab 94 and containing an in an open second shaped an S-shaped bridge 12 staple.

A reusable staple instrument 110 is shown above and adjacent to a cartridge 90 containing an S-shaped bridge 12 staple in its as implanted shape, FIG. 7. The instrument 110 has an extrusion mandrel 112 with an S-shaped face that matches the bridge of the staple and tab lock slots 114. When the instrument's extrusion mandrel 112 is advanced through the cartridge channel 92 it simultaneously disengages the staple retention tab 94 and extrudes the staple 12 from the cartridge 90 into bone. The O-shaped bridge 70 staple and cartridge 100 uses an O-shaped extrusion mandrel.

To support the surgeon and treat the patient, several reusable staple instruments 110 will be placed in a surgical tray with tens of cartridges 90 each containing a staple and ancillary instruments such as drill bits, drill guides, mallets, forceps, and impactor. This surgical tray is reusable, hospital cleaned and sterilized and replenished as implants are used or instruments damaged. These types of all-inclusive surgical trays are required for large surgical procedures involving multiple implants.

This reusable implant and instrument tray configuration is common to the market and prior art. Today's marketed staple systems all have at least one element that is reused and must be cleaned and sterilized by the hospital. This increases the cost of use and frequency of complication. Incomplete cleaning or sterilization can cause intra-patient disease transmission. This is most commonly an infection but can become of grave concern when the infection is antibiotic resistant or viral.

Figure 8:
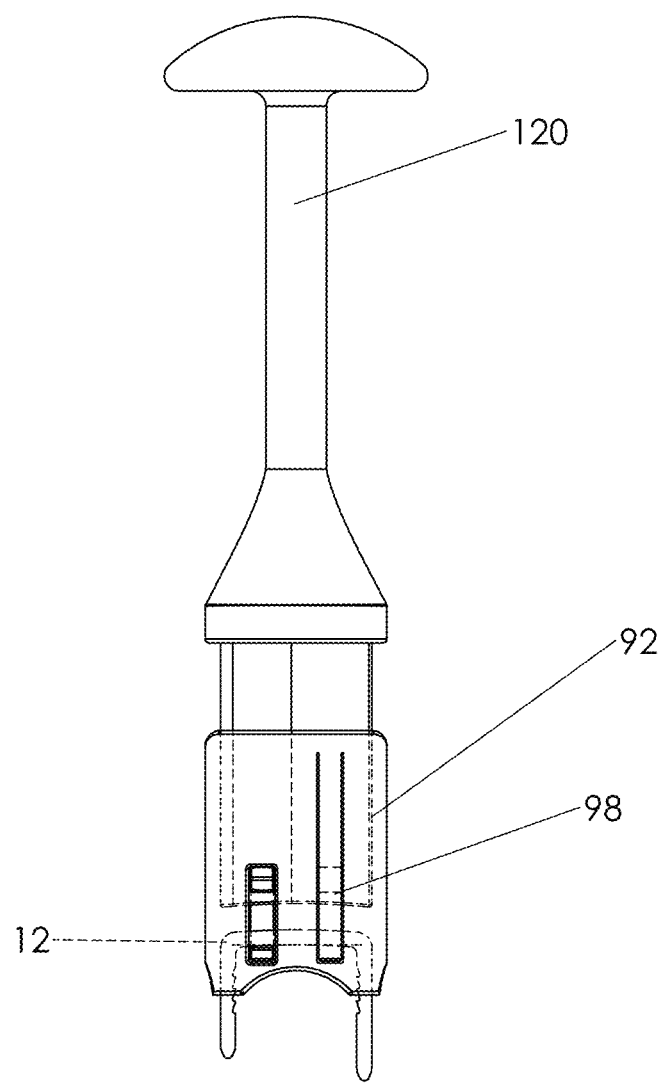
FIG. 8: Disposable staple extrusion instrument 120 with integrated cartridge 92 containing an open second S-shaped bridge 12 staple. A permanent retention tab 98 that locks the instrument 120 into the cartridge 92 while facilitating the extrusion of the staple 12.

To reduce hospital handling cost and minimize the incidence of hospital related infections embodiments of the subject invention can be built with a disposable staple instrument 120 combined with an integral S-shaped staple cartridge 92, as shown in FIG. 8. This embodiment can be delivered to the hospital in a quality controlled sterile package.

The integral instrument has an extrusion mandrel with an S-shaped face that matches the bridge of the staple and is assembled with the S-shaped bridge 12 staple of which both are within cartridge 92. When the instrument's extrusion mandrel 120 is advanced through the cartridge channel 92 it simultaneously disengages the staple retention tab 98 of the cartridge 92 and extrudes the staple from the cartridge 92 and into bone. The O-shaped staple and cartridge uses an O-shaped extrusion mandrel.

This pre-sterilized combination instrument, cartridge and implant can be packaged with a drill and drill guide so that the medical procedure kit fully supports the surgical technique. Hospital costs savings are achieved because there is no hospital cleaning or sterilization required and the patients and hospital benefit from fewer infections and patient complications.

Operation of the Invention

The staple embodiments are uniquely suited for fixation of materials that have a tendency to benefit from compression or shrink and withdraw so that the stapled structures lose contact. Without limiting the scope of the invention the illustrated embodiments are used for bone fixation. In bone surgery fragments, separated segments and segments requiring fixation are pulled together by the staple because it is inserted so that at least one of a plurality of legs is placed in two or more bone segments. This method of surgical use is common to bone staples.

Figure 9:
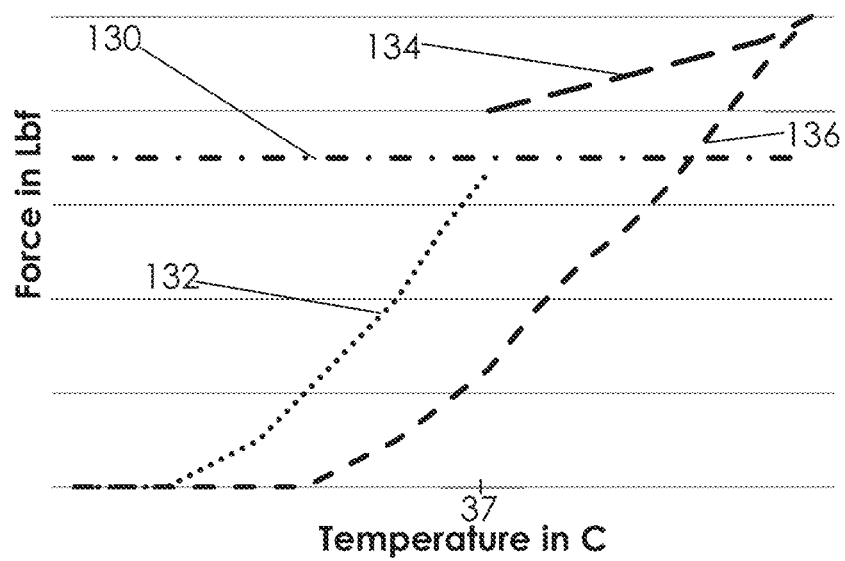
FIG. 9: Shape changing nitinol staple force vs. temperature curve shows a horizontal force versus temperature curve 130 for the staples embodiments of the subject invention and illustrates its compression force independence of temperature. Force versus temperature of nitinol staples heated with body temperature curve 132 is nonlinear and increases from below room to body temperature of 37° C. thus body temperature staples are changing shape with handling and not at full compression until the wound is closed and warmed. The nitinol staple force curve during electrical resistance heating 136 and environmental cooling 134 under the patented methods of Fox, U.S. Pat. No. 7,240,677 shows that known forces are achieved with electrical heating but the force can decrease due to subsequent environmental cooling and thus if not reheated just prior to skin closure these staples apply an unknown bone compression force if any.

The shape changing staples, of the embodiments of the subject invention, exert bone compression force that is not temperature dependent. This provides tremendous advantage for the surgeon and patient over prior art nitinol shape changing implants. The staple compression force versus temperature curve for three types of nitinol staples are shown in FIG. 9. The subject invention staple curve 130 showing force independent of temperature, a body temperature nitinol staple curve 132 and an electrically heated nitinol staple cooling 134 and heating 136 curve.

Temperature independence solves problems with the prior art nitinol staples because the embodiments of the subject invention apply consistent force prior, during and following implantation. Body temperature staple force changes as the operative wound warms from near room temperature to body temperature. This force increase occurs after the wound is closed and without the knowledge of the surgeon can create fracture or deformity. The electrical heated staple of Fox, U.S. Pat. No. 7,240,677 cool after heating and if not reheated just prior to wound closure can cool so that bone fixation forces decrease to zero. No fixation may result in poor healing and reoperation.

Figure 10:
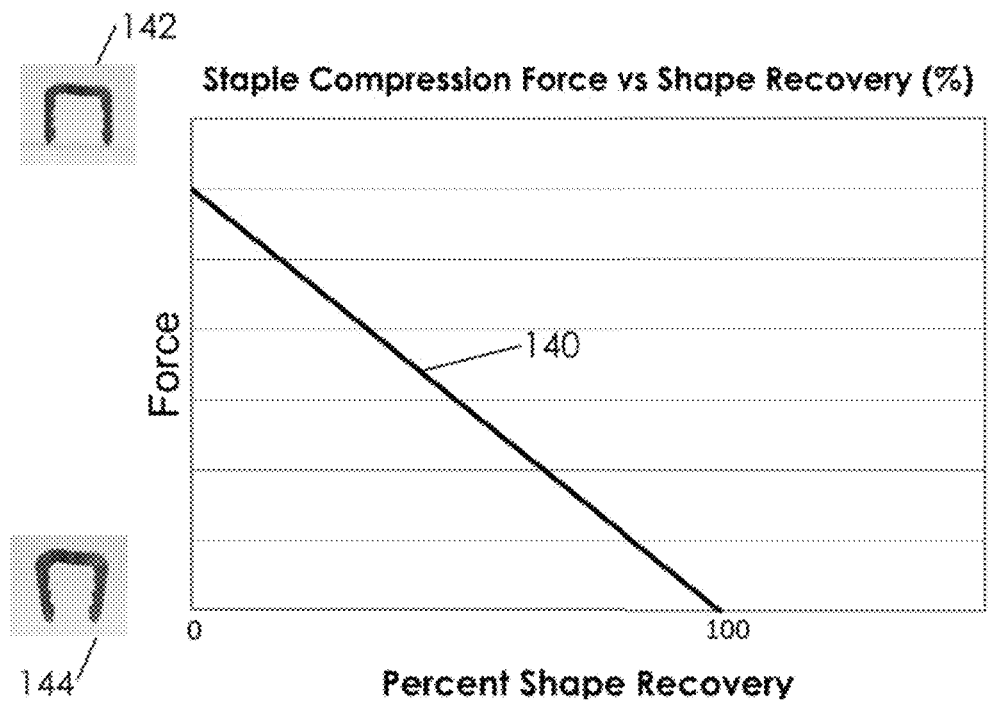
FIG. 10: Shape changing staple force vs. extent of shape change curve 140 shows that a staple in an open second shape 142 having not undergone any shape recovery imparts the maximum force bone. While a staple that has recovered 100% of its closed first shape 144 applies no compression force to bone.

The bone applied force curve 140 and percent staple first closed shape recovery for and embodiment of the subject invention is illustrated in FIG. 10. This illustration shows a reduction in staple shape change force with the extent of shape change. When the staple is in its open second shape with the legs parallel and the bridge fully extended 142 the bone compression force is maximum. When the staple has returned to its closed first shape 144 the force is zero and the bones have been pulled together to a maximum extent. The force versus shape recovery curve of the prior art staples is complicated due to its temperature dependence and thus no simple geometric relationship between the staple and bone compression force of the prior art.

The S-shaped or O-shaped staples are retained in the staple cartridge in a recoverable deformed state. The cartridge retains the staple in the open second shape from manufacturing assembly to patient implantation. The staple is held by the cartridge to store its mechanical shape changing energy. This mechanical energy is stored through the elasticity or the metal if stainless steel or other linear elastic metal (FIG. 11) or in a stress induced martensitic state (FIG. 12) if fabricated from nitinol or other material that exhibits this behavior. Once extruded from the cartridge the staple spontaneously acts to return to its first closed shape. This shape change pulls together and compresses bone.

Figure 11:
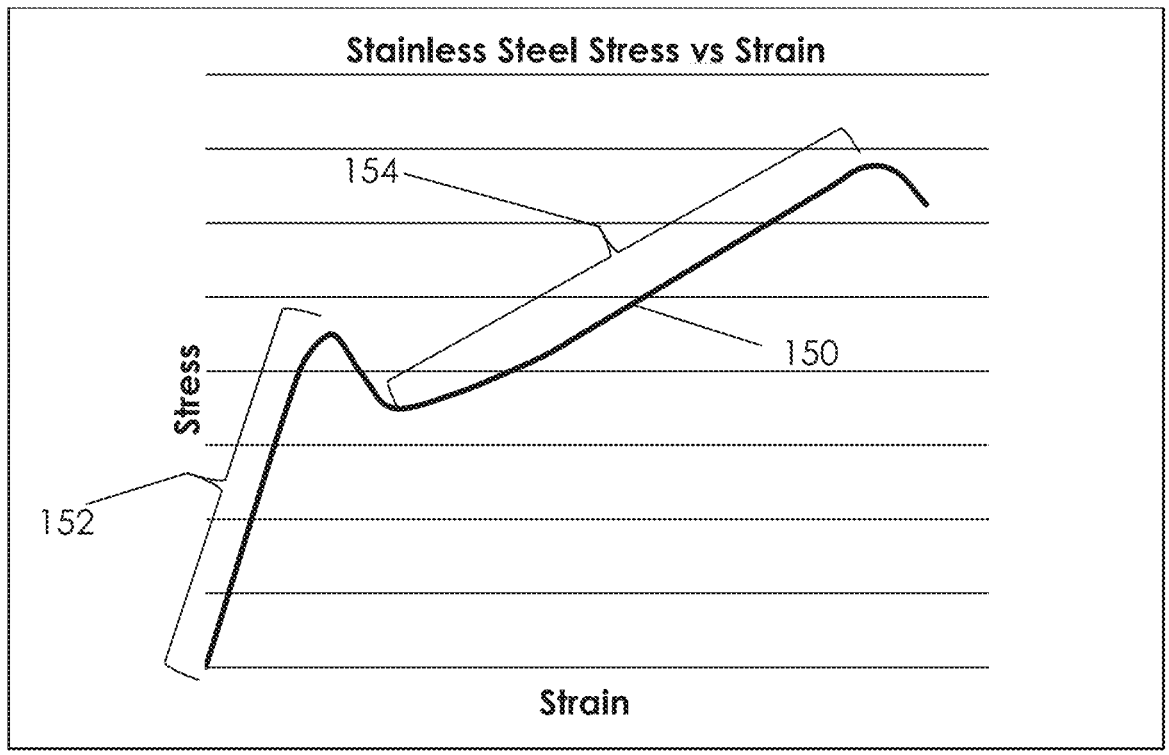
FIG. 11: Curve of stress versus strain 150 in materials such as stainless steel. The curve shows that materials that exhibit linear elastic behavior in a portion of their stress versus strain curves 152 can recover their shape and be used in the embodiments of the subject invention. Strain exceeding the elastic yield stress will plastically deform as is illustrated in the portion of the curve 154. Materials that plastically yield will retain some degree of elastic recovery and have a percent shape recovery available of greater than zero but less than 100% and thus can apply compressive force to bone.

Curve of stress versus strain 150 in materials such as stainless steel is shown in FIG. 11. Curve portion 152 of curve 150 shows the region where the deformation was primarily elastic (i.e., no substantial plastic deformation). Curve portion 154 of curve 150 shows the region where there was substantial plastic deformation. Curve portion 154 further shows that there is recoverable energy in this curve portion. As shown in curve 150, there will be a strain in which the stainless steel material breaks and no energy is recoverable (i.e., there is recoverable stain until the material breaks).

Figure 12:
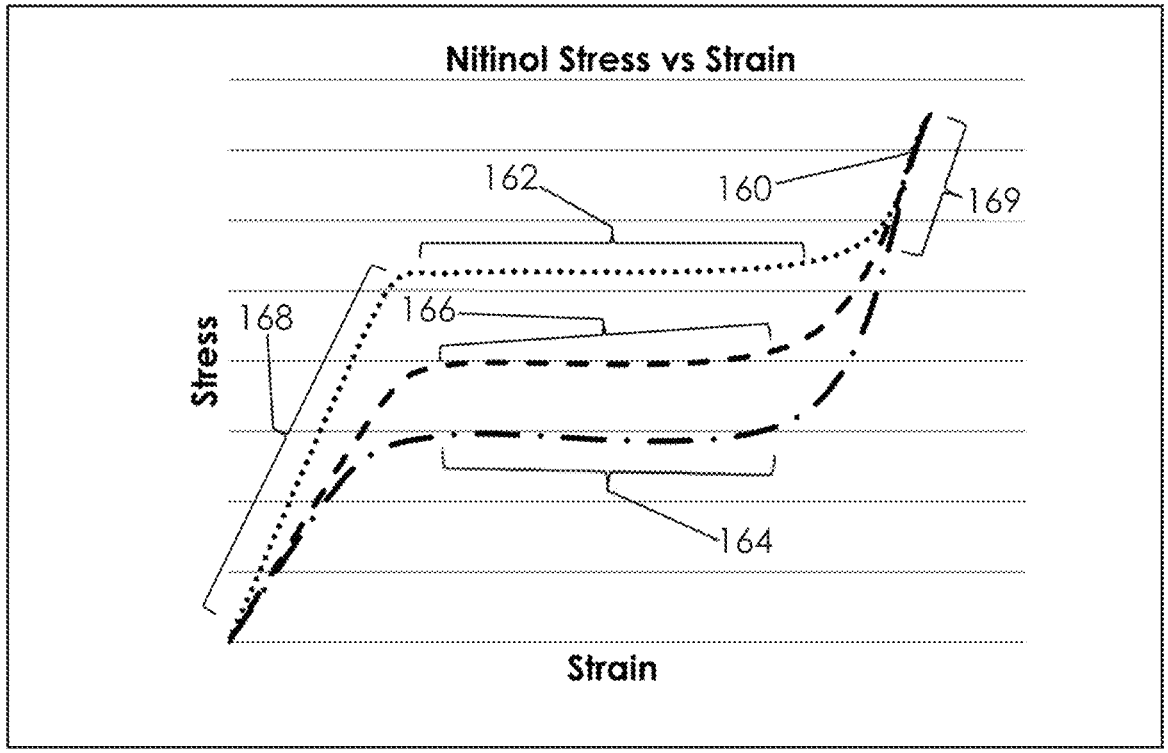
FIG. 12: Curve 160 of stress versus strain of nitinol showing its upper plateau stress region 162 if at room temperature and 164 if cooled below the martensitic transition temperature both regions associated with the creation of stress induced martensite as a part is strained. These plateaus are of the internal stress that must be overcome to strain the staple from the first closed shape to a second opened shape. The lower plateau stress region 166 is the internal stress that causes the staple to transition from its second open shape to its first closed shape. During this transition the staple uses this stored elastic energy to exert force on bony structures that resist it. With shape recovery the stress induced martensite reconverts to austenite as the staple works to transition to its first closed shape.

Curve 160 of stress versus strain of nitinol is shown in FIG. 12. Curve portion 168 of curve 160 shows the region where the deformation was primarily elastic. (i.e., no substantial plastic deformation and little to no substantial pseudo elastic deformation). Curve portion 162 of curve 160 shows the region where the deformation also includes pseudo elastic deformation. It is in this curve portion 162 of curve 160 that portions of staple (such as staple 10), including portions of its staple bridge and corners (such as staple bridge 12 and corners 50), would transform from austenite to martensite (i.e., the stress induced martensite). Curve portion 169 of curve 160 shows the region where there was substantial plastic deformation of the nitinol. While curve portion 169 further shows that there is recoverable energy in this curve portion, this curve portion is relatively short before the strain will break the nitinol.

Figure 13:
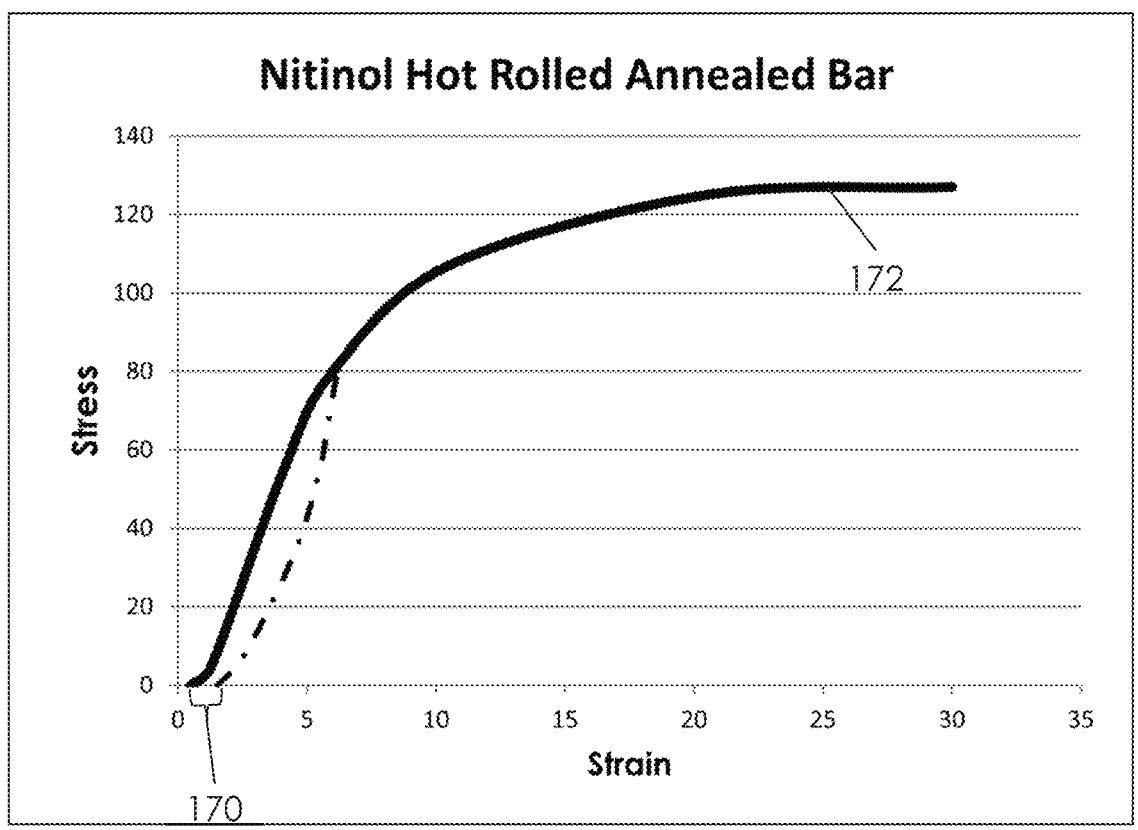
FIG. 13: Curve of stress versus strain of annealed nitinol (hot rolled annealed bar) (OAP BAR3-NITL-A-0.5100 NiTi-0.51011 diameter-hot rolled, straightened, centerless ground bar manufactured by from SAES Smart Materials, Inc. New Hartford, N.Y.).

Curve of FIG. 13 shows annealed nitinol (from SAES Smart Materials, Inc., New Hartford, N.Y.) and its lack of significant stress induced martensite and near pure super elastic and plastic behavior. In contrast to the cold worked nitinol characteristics of FIG. 12, no plateau stress is visible as would be seen with the creation of stress induced martensite. Consequently, based on the cold working of the material and its heat treatments the recoverable deformation of nitinol may be due to its super elasticity or the formation of stress induced martensite. In this material example the deformation is plastic along 172 beginning at about 6% strain and results in only 10% to 15% unrecoverable deformation 170 when released.

During surgical use the surgeon inserts the staple's leg into bone across a fracture or joint requiring fixation. The legs are either forced into bone through impaction or inserted into drilled holes matched to the diameter and separation between the staple legs. Once the staple legs are partially in bone the staple is then extruded from the cartridge. As the staple advances within the cartridge the staple legs begin to move inward pulling bone together and exerting compression forces. As the staple continues to advance the elastic energy acting to transition the staple from a second open shape to a first closed shape is transferred from the cartridge and to bone. This elastic energy converts to work to pull the bone together and apply residual compression force. Once the staple is fully extruded from the cartridge the staple applies its full force to pull together and compress bone. The transfer of shape changing forces from the cartridge to bone can be controlled by the staple and cartridge designs or the rate at which the surgeon extrudes the staple.

The operation of embodiments of the subject invention allow a novel and cost effective manufacturing technique and result in a stronger and more consistent implant. First, the operation of the embodiment is independent of temperature in the range of temperatures expected in clinical use. Thus tight control of the material's crystalline structure transition temperature is not required. Furthermore, the temperatures are set so that the material is always in its strong and high temperature austenitic form. Thus as long as the austenitic finish temperature is above 20° C. then it will be stable in the operating theater and patient's body. So fine chemistry control and post heat treatments to shift transition temperatures is not required.

To complement the temperature independent operational mode the implant is cut using three-dimensional inline cutting manufacturing methods from a block of material and not bent from an extruded wire or plate. Since the implant is not bent into a final form, stress concentrations in the material or changes in transition temperatures do not occur. Thus embodiments of the subject invention are stronger and less likely to fail from fatigue loading.

Together the manufacturing steps, requirement to retain the staple in the open second shape complement the ability to extrude the staple from the cartridge and together are designed to support the one operative task the surgeon must perform. That task is the advancement of the staple legs into bone. The surgeon does not to need to compress the staples with pliers, open the staple to fit into its drill holes, keep the staple on ice or heat it with electrical current as is required by the prior art. The surgeon needs only to put the tips of the legs of the staples into bone and advance the extrusion mandrel until the staple is fully implanted. The extrusion instrument can be pushed by hand or impacted with a mallet to fully seat the implant in bone. The extrusion instrument and cartridge can be formed with ergonometric features. The extrusion instrument can be reusable and receive staple cartridges or disposable and be an integral component to a staple cartridge.

CONCLUSIONS AND SCOPE

The embodiments illustrated in this application are a significant advancement over the prior art staples in: 1) the method of operation of the staple and its high strength, 2) the method of insertion of the staple, 3) its compressive force temperature independence, 4) its efficient staple retention and delivery system, 5) its compatibility with reusable or single use product configuration, 6) its efficient and cost effective manufacturing methods, and 7) its minimization of the steps required to place the device. These advantages are important to musculoskeletal surgery as well as industrial applications for staples.

Although the description above contains many specificities, these should not be construed as limiting the scope of the embodiments but as merely providing illustrations of some of the presently preferred embodiments. Thus the scope of the embodiment should be determined by the appended claims and their legal equivalents, rather than by the examples given.

The disclosures of all patents, patent applications, and publications cited herein are hereby incorporated herein by reference in their entirety, to the extent that they provide exemplary, procedural, or other details supplementary to those set forth herein.

What is claimed is:

1. A pre-sterilized kit comprising
   (a) a staple device that comprises
      (i) only one staple, wherein the staple is a bone staple that comprises
         (A) a staple bridge, wherein
            (I) the staple bridge comprises a shape memory metal in a first shape, wherein the first shape is an elongated shape of the staple bridge and the staple bridge is restrained in the first shape by a cartridge,
            (II) the staple bridge has a bridge shape such that when released from the cartridge, the bridge can move between the first shape and a second shape with no substantial plastic deformation of the staple bridge, wherein the second shape is a contracted shape of the staple bridge,
            (III) at least a portion of the shape memory metal has a crystalline structure in the form of martensite; and
         (B) a plurality of staple legs connected to the staple bridge, wherein
            (I) the plurality of staple legs comprise the shape memory metal,
            (II) the staple is operable for moving when released from the cartridge between a parallel shape and a non-parallel shape without substantial plastic deformation of the staple, wherein the non-parallel shape is a convergent shape,
            (III) the staple is in the parallel shape when the staple bridge is in the first shape and the staple legs are parallel, (IV) the staple is in the non-parallel shape when the staple bridge is in the second shape and the staple legs are not parallel and are convergent, and (V) the staple is operable for moving when the staple bridge and the plurality of staple legs are released from the cartridge to the non-parallel shape due to a transition of the crystalline structure of the shape memory metal from the martensite form to an austenite form without a change in temperature of the staple, and (ii) the cartridge having a channel in which the staple bridge is restrained in the first shape and in which the staple legs are restrained in the parallel shape, wherein the cartridge has a retention tab that locks the staple bridge in the channel restrained in the first shape and locks the staple legs in the channel restrained in the parallel shape, (b) an extrusion instrument that is configured to be movably coupled to the cartridge, wherein the extrusion instrument is operable for moving relative to the cartridge to extrude and release the staple from the cartridge while the extrusion instrument simultaneously disengages the retention tab, (c) a drill bit; and (d) a drill guide, wherein the staple, cartridge, extrusion instrument, drill bit, and drill guide are sterile.

2. The pre-sterilized kit of claim 1, wherein the staple-bridge has an S-shaped staple bridge shape.

3. The pre-sterilized kit of claim 1, wherein the staple-bridge has an O-shaped staple bridge shape.

4. The pre-sterilized kit of claim 1, wherein the shape memory metal comprises nitinol.

5. The pre-sterilized kit of claim 1, wherein the shape memory material can withstand a strain up to 6% with no substantial plastic deformation.

6. The pre-sterilized kit of claim 1, wherein the shape memory material can withstand a strain up to 8% with no substantial plastic deformation.

7. The pre-sterilized kit of claim 1, wherein the shape memory material can withstand a strain up to 13% with no substantial plastic deformation.

8. The pre-sterilized kit of claim 1, wherein the shape memory material can withstand a strain up to between 6% and 13% with no substantial plastic deformation.

9. The pre-sterilized kit of claim 1, wherein the staple bridge can withstand a strain up to 30% with no substantial plastic deformation.

10. The pre-sterilized kit of claim 1, wherein the pre-sterilized kit further comprises at least one ancillary instrument selected from the group consisting of mallets, forceps, and impactors.

11. A pre-sterilized kit of claim 1, wherein the pre-sterilized kit comprises a plurality of the staple devices.

* * * * *